US008485727B2

(12) United States Patent
Trouilly et al.

(10) Patent No.: US 8,485,727 B2
(45) Date of Patent: *Jul. 16, 2013

(54) MULTIPLE CHAMBER CONTAINER

(75) Inventors: Jean Luc Trouilly, Braine l'Alleud (BE); Freddy Desbrosses, Thuin (BE); Denis Bonnot, Rambouillet (FR); Christian Melin, Saint Remy les chevreuse (FR)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 1652 days.

This patent is subject to a terminal disclaimer.

(21) Appl. No.: 11/461,963

(22) Filed: Aug. 2, 2006

(65) Prior Publication Data
US 2007/0029001 A1 Feb. 8, 2007

Related U.S. Application Data

(60) Provisional application No. 60/704,555, filed on Aug. 2, 2005.

(51) Int. Cl.
*B65D 30/22* (2006.01)
*B65D 33/10* (2006.01)
*B65D 33/00* (2006.01)
*B65D 25/08* (2006.01)
*A61M 37/00* (2006.01)
*A61B 19/00* (2006.01)

(52) U.S. Cl.
USPC ............... 383/38; 383/9; 383/210; 206/219; 604/90; 604/410

(58) Field of Classification Search
USPC ...... 383/38, 93, 94, 39, 210, 211, 9; 206/828, 206/219; 141/114; 604/408–410, 82, 85, 604/87, 89, 90
See application file for complete search history.

(56) References Cited

U.S. PATENT DOCUMENTS

| 4,169,811 | A | 10/1979 | Yoshikawa et al. |
| 4,349,509 | A | 9/1982 | Yoshikawa et al. |

(Continued)

FOREIGN PATENT DOCUMENTS

| CA | 1075605 | 4/1980 |
| DE | 2742875 | 4/1979 |

(Continued)

OTHER PUBLICATIONS

Product Monograph; Primene 10% (Amino Acid) Injection; Baxter Corporation—Clintec Nutrition Division, Canada; revision Nov. 1997.

(Continued)

*Primary Examiner* — Jes F Pascua
(74) *Attorney, Agent, or Firm* — K&L Gates LLP

(57) ABSTRACT

A multiple chamber container for separately storing components of a parenteral nutritional formulation is provided. The multiple chamber container may include frangible barriers, preferably peelable seals separating the chambers from each other. The container preferably facilitates the selective activation of the peelable seals to permit the admixing of less than all the separately stored components. The container may include a chamber positioned at each of the opposite lateral ends of the container and at least one additional chamber between the lateral chambers. The at least one additional chamber may have a longitudinal length substantially less than the longitudinal length of at least one of the lateral chambers. This configuration allows for selective opening of the seals since when rolling the container from the top avoids pressurizing the at least one additional chamber and inadvertent activation of a seal. The longitudinal length of the at least one additional chamber may be from about two-thirds to about three-fourths the longitudinal length of at least one of the lateral chambers. Alternatively, the container may include a hanger flap extending from a top end of the container towards the bottom end a substantially greater distance relative to the at least one additional chamber than the lateral chambers.

10 Claims, 13 Drawing Sheets

U.S. PATENT DOCUMENTS

| | | | | |
|---|---|---|---|---|
| 4,467,588 | A | * | 8/1984 | Carveth ............... 53/425 |
| 4,526,752 | A | | 7/1985 | Perlman et al. |
| 4,602,910 | A | * | 7/1986 | Larkin ............... 604/87 |
| 4,608,043 | A | * | 8/1986 | Larkin ............... 604/87 |
| 4,952,068 | A | * | 8/1990 | Flint ............... 366/337 |
| 5,096,813 | A | | 3/1992 | Krumhar et al. |
| 5,207,509 | A | * | 5/1993 | Herbert ............... 383/38 |
| 5,260,023 | A | | 11/1993 | Evans, II |
| 5,287,961 | A | * | 2/1994 | Herran ............... 206/219 |
| 5,358,876 | A | | 10/1994 | Inoue et al. |
| 5,549,905 | A | | 8/1996 | David et al. |
| 5,766,621 | A | | 6/1998 | Timbo et al. |
| 5,928,213 | A | * | 7/1999 | Barney et al. ............... 604/410 |
| 6,074,366 | A | * | 6/2000 | Rogers et al. ............... 604/410 |
| 6,093,572 | A | | 7/2000 | Stenholm et al. |
| 6,319,243 | B1 | * | 11/2001 | Becker et al. ............... 604/410 |
| 6,399,387 | B1 | | 6/2002 | Stenholm et al. |
| 6,468,259 | B1 | * | 10/2002 | Loretti et al. ............... 604/410 |
| 6,561,008 | B1 | | 5/2003 | Mulholland et al. |
| 6,627,443 | B1 | | 9/2003 | Stenholm et al. |
| 6,676,901 | B1 | | 1/2004 | Hatakeyama et al. |
| 7,169,138 | B2 | * | 1/2007 | Becker et al. ............... 604/410 |
| 7,175,614 | B2 | * | 2/2007 | Gollier et al. ............... 604/410 |
| 7,546,918 | B2 | * | 6/2009 | Gollier et al. ............... 206/219 |
| 2002/0058927 | A1 | * | 5/2002 | Becker et al. ............... 604/518 |
| 2003/0036743 | A1 | * | 2/2003 | Becker et al. ............... 604/410 |
| 2003/0082823 | A1 | | 5/2003 | Sumitani et al. |
| 2004/0078023 | A1 | * | 4/2004 | Gollier et al. ............... 604/410 |
| 2004/0134802 | A1 | * | 7/2004 | Inoue et al. ............... 604/410 |
| 2005/0049157 | A1 | | 3/2005 | MacDonald et al. |
| 2005/0085577 | A1 | | 4/2005 | Ching et al. |
| 2008/0004594 | A1 | * | 1/2008 | Pahlberg et al. ............... 604/410 |
| 2008/0017543 | A1 | * | 1/2008 | Pahlberg et al. ............... 206/532 |

FOREIGN PATENT DOCUMENTS

| | | |
|---|---|---|
| DE | 19641909 | 4/1998 |
| EP | 0 101 185 B2 | 5/1990 |
| EP | 0 735 368 A1 | 10/1996 |
| EP | 0 524 021 B1 | 9/1997 |
| EP | 1 621 178 A1 | 2/2006 |
| EP | 1621178 A1 | 2/2006 |
| GB | 1 516 738 | 7/1978 |
| WO | WO 97/37628 | 10/1997 |
| WO | WO 98/10733 A | 3/1998 |
| WO | WO 2005/032968 A | 4/2005 |
| WO | WO 2004/080595 | 9/2009 |

OTHER PUBLICATIONS

International Search Report for International Application No. PCT/US2006/030051 mailed Mar. 19, 2007.

International Search Report for International Application No. PCT/US2006/030058 mailed Dec. 13, 2006.

* cited by examiner

At 25°C/40%RH:

At 30°C/35%RH:

MULTIPLE CHAMBER CONTAINER

This application claims the benefit of U.S. Provisional Application Ser. No. 60/704,555 filed on Aug. 2, 2005.

BACKGROUND OF THE INVENTION

The present invention is directed generally to medical solutions, containers for storing medical solutions and oxygen indicators for detecting the presence of oxygen in a medical container More particularly, the present invention is directed to ready-to-use ternary parenteral nutritional formulations for certain patient populations, particularly fluid limited populations, the container systems for long-term storage and selective administration of such formulations and oxygen indicators for such container systems. More specifically, the present invention is directed to such formulations being stored in flexible containers having multiple chambers for isolated long-term storage of the various nutritional components of such formulations, oxygen indicators for alerting healthcare professionals of an oxygen compromised container and containers facilitating selective sterile admixing into a ready to infuse formulation and administration of such formulation. Even more specifically, the invention is directed to multi-chamber containers allowing selective admixing of two or more solutions contained in the chambers such as nutritional solutions of lipids, carbohydrates, amino acids and electrolytes and oxygen indicators able to withstand heat sterilization and having acceptable storage characteristics.

Medical solutions such as parenteral and enteral nutrient solutions, dialysis solutions, pharmacological solutions, and chemotherapy solutions are routinely stored in a variety of containers made of glass or plastic. While glass containers offer many benefits such as gas impermeability and virtually complete compatibility with medical solutions, glass containers are heavy, easily broken, difficult to handle and can release aluminum into the solutions. As a result, more and more medical solutions are being stored in plastic containers Flexible containers such as bags made from plastic films have gained increased acceptance.

Frequently the prescription to be administered to a patient is comprised of components which are not compatible for long storage periods. One method of overcoming this limitation is to combine or compound the components just prior to administration. Such compounding may be accomplished manually or with automated compounders. However such a combination method is time consuming, may give rise to errors in formulation and increases the risks of contamination of the final mixture.

To overcome the drawbacks of long term incompatibility and reduce the risks of compounding, flexible containers can be formed with multiple chambers for separately storing medical solutions. These bags are formed with frangible connections or peal seals which provide for mixing of the all the contents of the chambers by manipulation of the connections or seals. A drawback of utilizing such multi-chamber containers is that one is restricted to the formulation which are provided by the supplied components and proportional amounts which are housed in the various chambers. When seeking to address the needs of varying patient populations, particularly fluid restricted populations, such restriction may hinder the ability to utilize such a containers, cause use of only a portion of the contents of such a container or cause multiple versions of such containers to be stored.

As described previously, flexible containers having multiple chambers such as multi-chamber bags have separation means that permit communication and mixing of the separately stored components or solutions. Some such multiple chamber containers utilize frangible valves while others use a score line or line of weakness in the barrier separating the chambers to effect mixing of the separately stored components. Still others use tear strips or tear tabs. More advantageous multi-chamber containers in terms of cost and ease of use are of the type which include peel seals formed by heat or radio frequency sealing of the two sheets of thermoplastic material that comprise a flexible bag to define multiple interior chambers. The heat seal provides a barrier that is resistant to unintentional opening forces but is openable with the application of a specific force. These types of multiple chamber containers are disclosed in U.S. Pat. No. 6,319,243 which is incorporated herein by reference.

Plastic containers such as those just discussed however can also present unique issues which must be addressed. One possible issue is that heat sterilization such as autoclaving can affect certain plastic materials used to form the container and/or the heat seal separating the chambers. Another possible issue is that certain plastic materials are permeable to atmospheric oxygen and may inadequately protect oxygen sensitive solutions or components. Yet another is that certain fat soluble or lipophilic solutions or components may not be compatible with certain plastic materials. For example, lipid formulations such as Lipid emulsions used in parenteral nourishment cannot be stored in certain plastics because it can leach out some plastic material from the container, The lipid emulsion would be contaminated and the plastic containers integrity can be compromised.

Lipid emulsions are generally one component of a parenteral nutritional solution (PN). Ternary parenteral nutritional formulations are used to provide all the nutritional components required by a patient. These PN formulations include also a carbohydrate component, an amino acid component, vitamin, trace element and electrolytes components. Because of various incompatibilities, nutritional components of PN formulations are prime examples of medical solutions that cannot be stored long term as a mixture in a ready-to-use state. They can only be combined in a relatively short time period prior to administration.

The individual constituents of each component should be determined by the nutritional recommended requirements of the particular patient population to be treated. For example, PN formulations for adult patients may have different constituents in each component or at least different amounts of each constituent than PN formulations for infants. Moreover, preparation of the separate components of PN formulations for premature infants, neonatal patients or small children presents unique problems. For one, the volume of fluid that may be infused into such patients is relatively small. Seeking to provide all of the desired nutritional components in such a low volume is extremely difficult. For example, the concentration ranges for individual constituents of certain component solutions must be narrowly constricted In addition, some of the individual constituents are either interdependent or incompatible if present in certain forms and concentrations. For example, the breadth of the acceptable concentration range for magnesium for a premature infant is about 0.2 mmol. In other words, the difference between the lowest acceptable concentration of magnesium and the highest acceptable concentration of magnesium is 0.2 mmol. In addition, there is a limit to the amount of chloride a premature infant can tolerate; so in an attempt to provide the required amount of certain electrolytes such as magnesium and calcium as a chloride, the chloride maximum may be exceeded. Furthermore, electrolytes such as calcium and phosphate may be incompatible in certain concentration levels.

Also, storing the components of a PN formulation in a single or multi-chamber plastic container for sterile mixing to form the PN formulation also presents unique problems. As already discussed above, the lipid component is incompatible with certain plastic material In addition, some of the components are sensitive to oxygen which can permeate through certain plastics. Overwraps or overpouches are typically used to restrict the ability of oxygen to get to the multi-chamber containers; however, the overwrap may still allow a small amount of oxygen to diffuse through. In addition, the overwrap may develop a leak which would allow an excessive amount of oxygen to be exposed to the container. Such a leak may not be visible and the presence of such oxygen needs to be indicated to the health care provider, While oxygen indicators exist they appear to not be able to withstand heat sterilization and still function properly after prolonged storage. In other words, the oxygen indicator should be able to indicate the presence of oxygen (oxidized form or positive result) such as with a change in color that is distinguishable from the condition indicating a lack of presence oxygen (reduced form or negative result). Additionally, the oxidized and reduced colors of the indicator should not fade or alter after prolonged storage so as to create uncertainty as to the result.

Furthermore, certain amino acids with thiol function, such as cysteine or acetyl-cysteine can form hydrogen sulfide as a decomposition product during sterilization. An excessive level of hydrogen sulfide may negatively affect some of the nutritional components. Moreover, while the all the separately stored components are mixed to form the final PN formulation prior to administration, there are circumstances when it is undesirable to include one or more of the components found in one of the chambers in the final solution. For example, it may be desirable to not include the lipid component in the final solution for infants under septic status, coagulation abnormalities, high bilirubin level or for other reasons.

Therefore, there is a need for a flexible multiple chamber container that facilitates selective opening of one but not another frangible barrier, less than all the frangible barriers or the frangible barriers in a sequential manner.

There is also a need for individual components of a PN formulation that meets the recommended volume and nutritional requirements for certain patient populations and in particular infants or small children at different stages of development.

In addition, there is a need for means of providing a reliable indicator that atmospheric oxygen may have contaminated the contents of the container, a low level of hydrogen sulfide in case the formulation contains cysteine or derivatives amino acids and an oxygen absorber to eliminate residual oxygen in the overpouch. It would be desirable to provide absorbers and/or indicators that can withstand heat sterilization and prolonged storage and still possess the ability to indicate that an unacceptable amount of oxygen has been exposed to the container.

SUMMARY OF THE INVENTION

In a first aspect of the present invention a flexible container for storing medical products is provided. The flexible container comprises a plurality of adjacent chambers, a first chamber positioned at one lateral end of the container, a second chamber positioned at an opposite lateral end of the chamber and at least one additional chamber positioned between the first and second chambers; a first frangible barrier separating the first chamber from the at least one additional chamber and a second frangible barrier separating the second chamber from the at least one additional chamber; at least two ports located at one end the container; each port providing fluid communication with a different one of the first, second and at least one additional chambers; and a longitudinal length of the at least one additional chamber being substantially less than at least one of a longitudinal length of the first and second chamber.

In a second aspect of the present invention a multilayer flexible container for storing medical products is provided. The multilayer flexible container comprises: a first end and a second end; a first chamber positioned at one side end of the container, a third chamber positioned at an opposite side end of the container, and a second chamber positioned between the first and third chambers; a first frangible barrier between the first and second chambers and a second frangible barrier between the second and third chambers; a first port positioned at the second end of the container and providing fluid communication with one of the first and second chamber, and a second port positioned at the second end of the container and providing fluid communication with the third chamber; a hanger portion extending from the first end of the container, the hanger portion defining a border of each of the first, second and third chambers, the hanger portion extending towards the second end a substantially greater distance with respect to at least the second chamber than any of the other of the at least second chamber.

In a third aspect of the present invention a flexible multilayer bag for storing and admixing medical products is provided. The multilayer bag comprises: top, bottom, first and second lateral sides; a first chamber, a second chamber, and a third chamber; a first frangible barrier separating the first and second chambers and a second frangible barrier separating the second and third chambers; and at least two ports located at the bottom side, each port providing access to a different one of the first, second, and third chambers; wherein the first, second and third chambers are arranged such that rolling the bag from the top side activates one of the first and second frangible barriers before activating the other of the first and second frangible barriers.

In a fourth aspect of the present invention a flexible multilayer bag for storing and admixing medical products is provided. The flexible multilayer bag comprises: top, bottom, left, and right sides; a first chamber, a second chamber, and a third chamber; a plurality of frangible barriers separating the first, second and third chambers from each other; and at least two ports located at the bottom side, each port providing access to a different one of the first, second, and third chambers; wherein the first, second and third chambers are arranged such that rolling the bag starting at an intersection between the top side and one of the left and right sides allows sequential activation of the frangible barriers.

DETAILED DESCRIPTION OF THE INVENTION

In one embodiment of the present invention, there is provided a flexible multiple chamber container for separately storing medical solutions prior to use and facilitates selective activation of the frangible barriers separating the chambers. The container is preferably constructed to permit the storage of aqueous or lipid formulations without the leaching issues discussed above and to facilitate selective opening of the frangible barriers separating the chambers.

Figure 1:
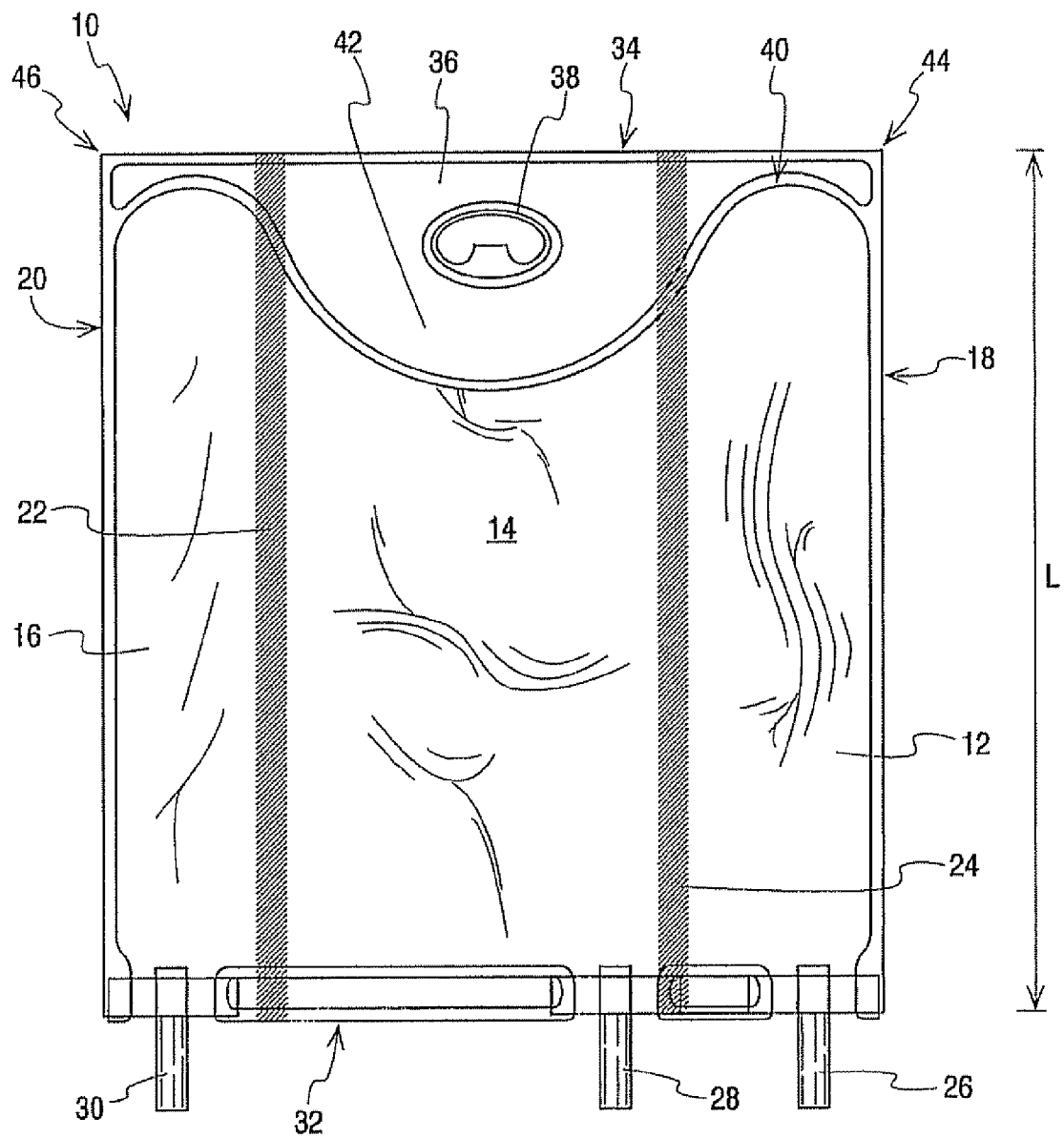
FIG. 1 is a plan view of one embodiment of a 300 ml container of the present invention.

FIG. 1 illustrates one embodiment of a multiple chamber container of the present invention. Preferably, the container 10 which is configured as a bag includes three adjacent chambers or chambers 12, 14, and 16. Chamber 12 is located at a lateral or side end 18 and chamber 16 is located at an opposite lateral or side end 20. The three chambers 12, 14, and 16 are preferably designed to hold aqueous solutions and/or lipid emulsions. As illustrated in FIG. 1, container 10 has a total fluid capacity of 300 ml with chamber 12 having a fluid capacity of 80 ml, chamber 14 having a capacity of 160 and chamber 16 having a capacity of 60 ml.

Figure 2:
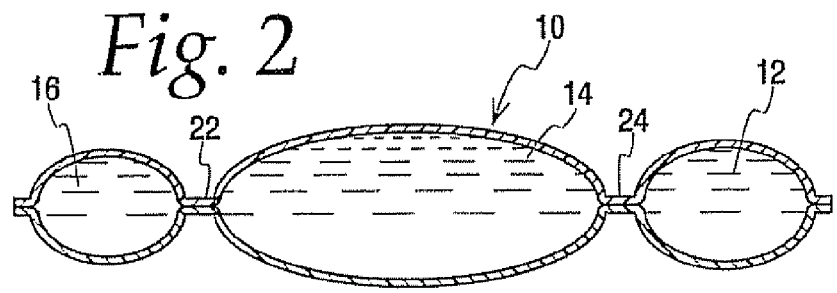
FIG. 2 is a cross sectional view of the container of FIG. 1.

Preferably, frangible barriers or openable seals 22 and 24 are used to separate the chambers. FIG. 2 shows a cross-section of container 10 and illustrates how the openable seals 22, 24 separate the formulations contained in chambers 12, 14, 16. The openable seals may be in the form of peel seal or frangible seals. The openable seals permit formulations to be separately stored and admixed just prior to administration thereby allowing storage in a single container of formulations which should not be stored as an admixture for an extended period of time. Opening of the seals allows communication between the chambers and mixing of the contents of the respective chambers. While containers having frangible seals are known, it is very difficult if not impossible to selectively open only one or less than all the seals using the typical method of rolling the multi-chamber bag. Selective activation of the seals is desirable because there are occasions when one of the formulations of a three formulation container is not to be administered. The selective opening of the seals will be discussed in more detail below.

Container 10 also preferably includes ports 26, 28, and 30 at the bottom end 32 of the container to provide communication with chambers 12, 14, and 16 respectively. One or more of the ports can be constructed for use as an additive port to allow the addition of materials such as micronutrients and/or can be constructed as administration ports. Preferably, the port his 28 is an administration port and includes a membrane that can be pierced by a cannula or spike of an administration set to deliver the contents to a patient and port 26 is for additions. In an alternate embodiment, there are two administration ports 28, 30 such that the admixture of formulations housed in chambers 12, 14 such an admixture of amino acid and glucose solution can be administered separately or at a different rate from the formulation housed in chamber 16 such as a lipid emulsion if desired. Of course, any number of ports can be used. In addition, the ports may be positioned in any number of ways; however it is preferred that the access ports are located on the same end of the container to permit more efficient manufacturing and filling of the chambers. In a further embodiment, one of the seals 22, 24 is made openable or peelable while the second seal is made permanent. This allows two of the chambers to be mixed while one of the chambers stays separated permanently. The admixture and separated solution may then be administered separately without requiring selective activation of the openable seals. Administration ports are then provided on two of the chambers such that one administration port is provided so that the chamber separated by the permanent seal may be administered while a second administration port is provided to allow the admixture to be administered.

At the top end 34 of the container 10, preferably opposite end 32 where the administration port(s) are located, there is provided a hanger portion 36 which in the embodiment shown in FIG. 1 is a flap having a centrally located hole 38 for hanging the container. The flap 36 defines a border 40 of the upper end of all the chambers 12, 14, and 16. The central portion 42 of the hanger flap 36 preferably extends a substantial distance towards the bottom end 32 of the container 10, more preferably about one-fourth the longitudinal length L of the container 10 and even more preferably about one-third of the length L of the container 10. Preferably, the flap 36 extends a greater distance towards the bottom end 32 at least at the central chamber 14 and can also extend a greater distance towards the bottom end 32 at the central chamber 14 and at one of the other chambers 12, 16. This extra extension of the flap 36 with respect to center chamber 14 results in chamber 14 having a shorter longitudinal length than the longitudinal length of lateral or side end chambers 12, 16. The longitudinal length of central chamber should be from about two-thirds to about three-quarters the longitudinal length of at least one of the lateral end chambers. This configuration allows for selective opening of the seals as will be discussed below. The longitudinal length of the chambers is measured from their respective top borders to their respective bottom borders. For curved or irregular borders the longitudinal length is the average of the longitudinal lengths taken continuously across the border.

Before addressing how the configuration of the chambers 12, 14, 16 and/or hanger flap 36 facilitates selective opening of the seals 22, 24 chambers it would be instructive to describe the typical method of opening the seals 22, 24.

Figure 3:
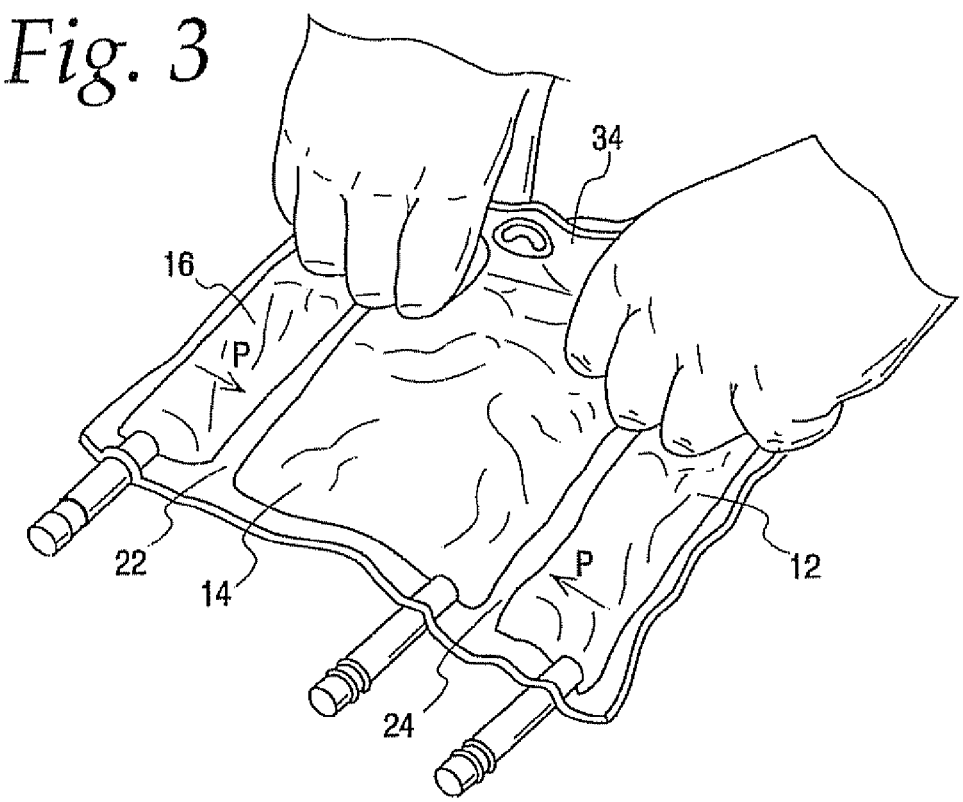
FIG. 3 shows a typical rolling method for opening all the seal of a container having multiple chambers.

FIG. 3 illustrates the typical rolling method of opening the seals 22, 24 to mix the contents of chambers 12, 14, and 16, The hanger flap 36 or top end 34 is rolled over itself in a squeezing motion. In multi-chamber bags where all the chambers extend substantially the same distance from their respective bottom borders to their respective top borders, rolling the bag would pressurize all the chambers too much risking unintended activation of the wrong seal. Also, multi-chamber bags having a central chamber that extends a greater distance from its bottom border to its top border than the other lateral end chambers, rolling of the bag would pressurized the central chamber and randomly activate one or more seals bordering the central chamber. Multi-chamber containers of the present invention however include chamber arrangements to facilitate selective activation of the seals.

In container 10, chamber 14 does not extend as far towards the top end 34 as do chambers 12 and 16, i.e. chamber 14 is about thee-fourths the longitudinal length of the other chambers 12, 16; therefore rolling the bag from the top end 34 only pressurizes chambers 12 and 16. In order to selectively activate only one of the seals 22, 24, only the end chamber adjacent to the seal desired to be activated is squeezed with a continuation of the rolling motion. Because of the extend of the hanger flap 36, the central chamber 14 is not pressurized preventing the activation or partial activation of the second peel seal. Further rolling and squeezing of the opposite lateral end chamber would activate the other seal. In this manner sequential activation of the seal is possible with containers of the present invention. Accordingly, the formulation which on occasion may not be administered should therefore be housed in one of the chambers located at the lateral ends of the container.

Specifically, if the user wanted to activate only seal 24, the user may start rolling the bag 10 at the top end 34. Without pressurizing chamber 14, the user can squeeze the bag at the location of chamber 12. Once seal 24 is activated, the user can stop rolling and squeezing. If the user wanted both seals 22, 24 activated instead, bag 10 can be rolled starting at the top end 34 while squeezing down on both end chambers 12, 16.

Figure 4:
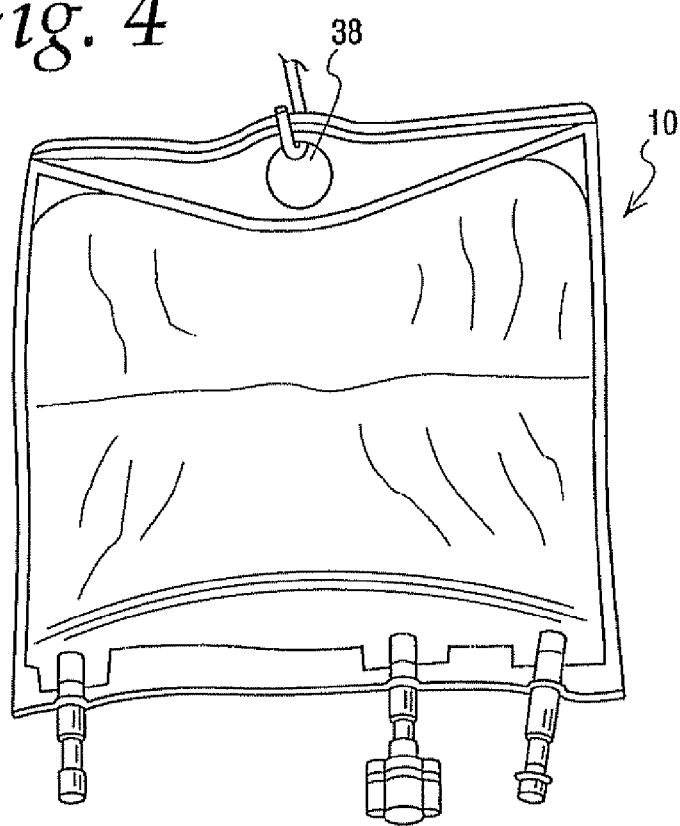
FIG. 4 is a plan view of the container of FIG. 1 after activation of peel seals.

Referring briefly to FIG. 4 after the seals 18 and 20 have been opened the contents of the container 10 may be mixed by manipulation of the container and then administered to the patient by first hanging the bag from a hook using hole 38.

Another rolling technique is also used to activate the seals of multi-chamber bags. Referring to FIG. 1, this technique also uses a rolling motion except instead of starting at the top end 34, container 10 is can be rolled starting at one of the top end corners 44, 46. Again in multi-chamber bags where all the chambers extend substantially the same distance from the bottom, i.e. have substantially equal longitudinal lengths or bags having a central chamber that extends a greater distance from the bottom to the top end than the other end chambers, i.e. a central chamber having a longitudinal length greater than either of the other chambers, rolling from a corner produces too much pressure on a central chamber risking the unintended activation of the wrong seal. Using this corner rolling method with containers of the present invention would not result in the activation of an unintended seal or at least not occur as often.

In the chamber arrangement of container 10, selective activation of seal 24 using the corner rolling technique is as follows. Container 10 is rolled starting at corner 44. The rolling would continue until chamber 12 is sufficiently pressurized enough to cause seal 24 to activate. Chamber 12 can also be squeezed in order to prevent rolling the container too far. Since chamber 14 does not extend towards the top end 34 as far as chamber 12, the rolling is not enough to pressurize chamber 14 to the degree necessary to activate seal 22 by the time seal 24 is activated. Therefore, if chamber 14 were to extend the length of the container to the same degree as chambers 12, much more attention and care would have to be exercised to prevent inadvertent pressurizing of chamber 14 if it could be accomplished at all.

Figure 5:
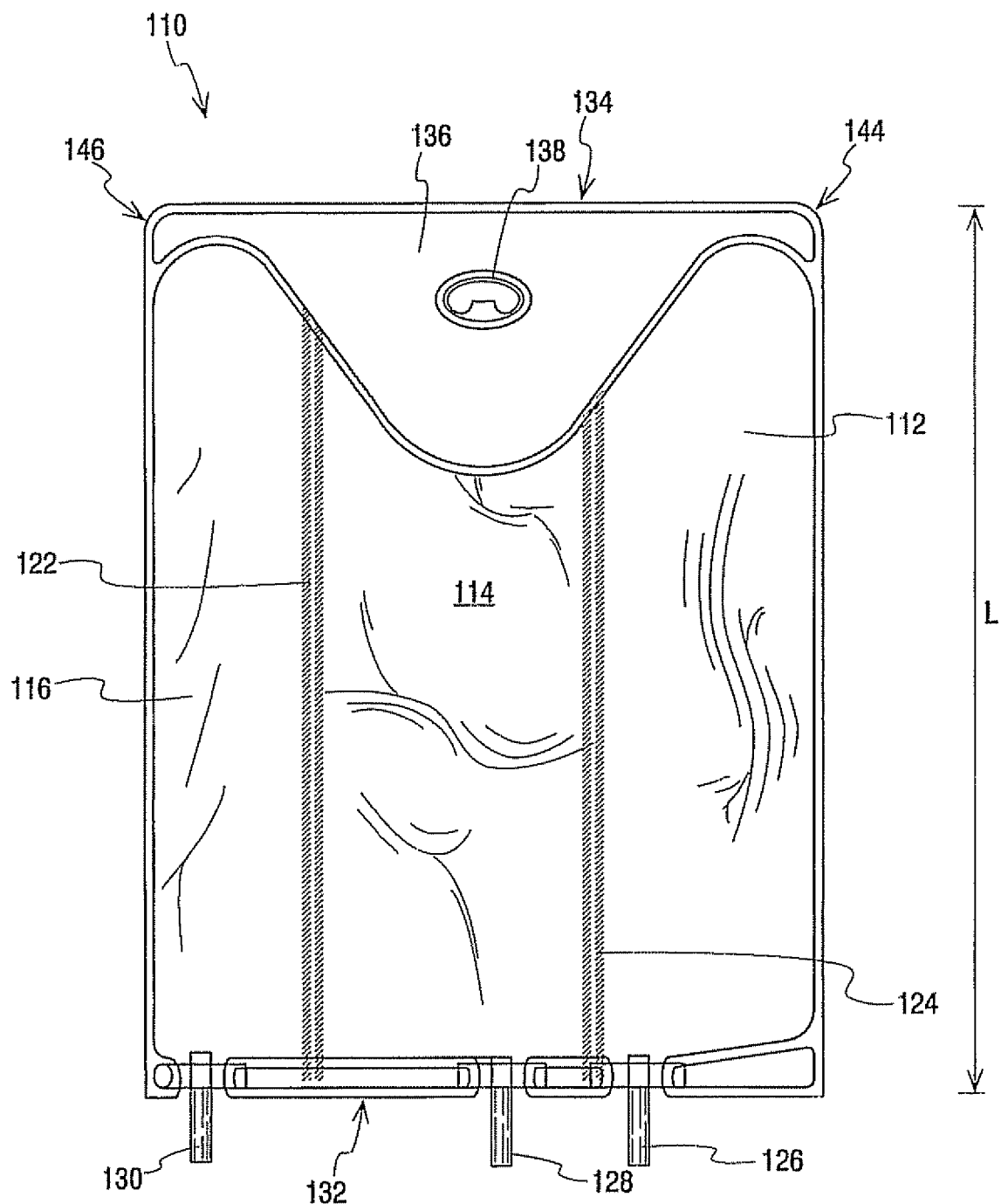
FIG. 5 is a plan view of one embodiment of a 500 ml container of the present invention.
Figure 6:
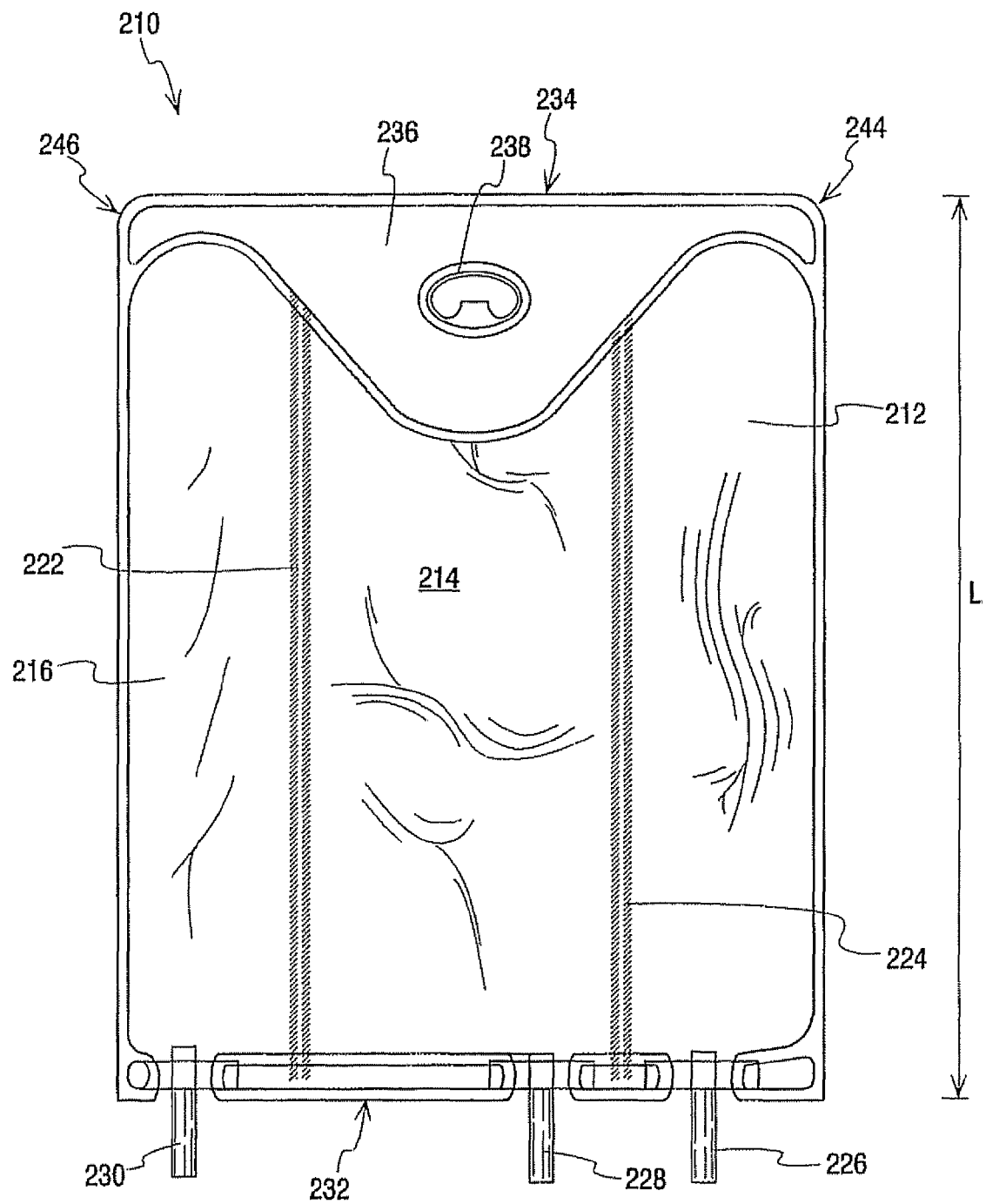
FIG. 6 is a plan view of one embodiment of a 1000 ml container of the present invention.

Two other embodiments of the container of the present invention are shown in FIGS. 5 and 6. Containers 110 and 210 shown in FIGS. 5 and 6, respectively also include three chambers 112, 114, and 116 and 212, 214, and 216 respectively. Containers 110 and 210 are constructed using the same materials and similar methods as those used in container 10. The only significant difference is the size and capacity of the containers 10, 110, and 210. As illustrated in FIG. 5, in a preferred embodiment, container 110 has a fluid capacity of 500 ml with chamber 112 having a fluid capacity of 221 ml, chamber 114 having a capacity of 155 ml and chamber 116 having a capacity of 124 ml.

As illustrated in FIG. 6, in a preferred embodiment container 210 has a fluid capacity of 1000 ml with chamber 212 having a fluid capacity of 392 ml, chamber 214 having a fluid capacity of 383 ml, and chamber 216 having a fluid capacity 225 ml.

Containers 110 and 210 also preferably include peelable seals 122 and 124 and 222, 224 respectively which separate the chambers and permit opening of the chambers to allow communication between the chambers and admixing of the contents of the respective chambers. Both containers 110 and 210 also include hanger flaps 136 and 236 including hanger holes 138 and 238, respectively.

Just as container 10, containers 110 and 210 have hanger portions or flaps and chambers that are configured to facilitate selective activation of the seals. For example, containers 110, 210 both have hanger flaps 136, 236 that extend towards bottom ends 132, 232 (about one fourth to about one-third the longitudinal length of the container 110, 210) respectively more so with respect to central chambers 114, 214. Consequently, the majority of the area of chambers 114, 214 have a longitudinal length that is about two-thirds to about three-quarter less than the longitudinal length of the majority of the area of their respective lateral end chambers 112, 116 and 212, 214. Rolling containers 110, 210 starting at the top ends 134, 234, or one of corners 144, 146, 244, 246, respectively allows rolling of the containers 110, 210 and squeezing of the chamber adjacent to the seal desired to be selectively activated without undue pressure being placed on the central chambers 114, 214 which could cause unintended activation of the other seal.

Containers 110 and 210 also include access ports 126, 128, and 130, and 226, 228, and 230, respectively. These ports are constructed using the same materials and in a similar manner as access ports 26, 28, and 30. To permit the same equipment to fill containers 10, 110, and 210 it is preferable to position so to be the same distance from each other.

Figure 7:
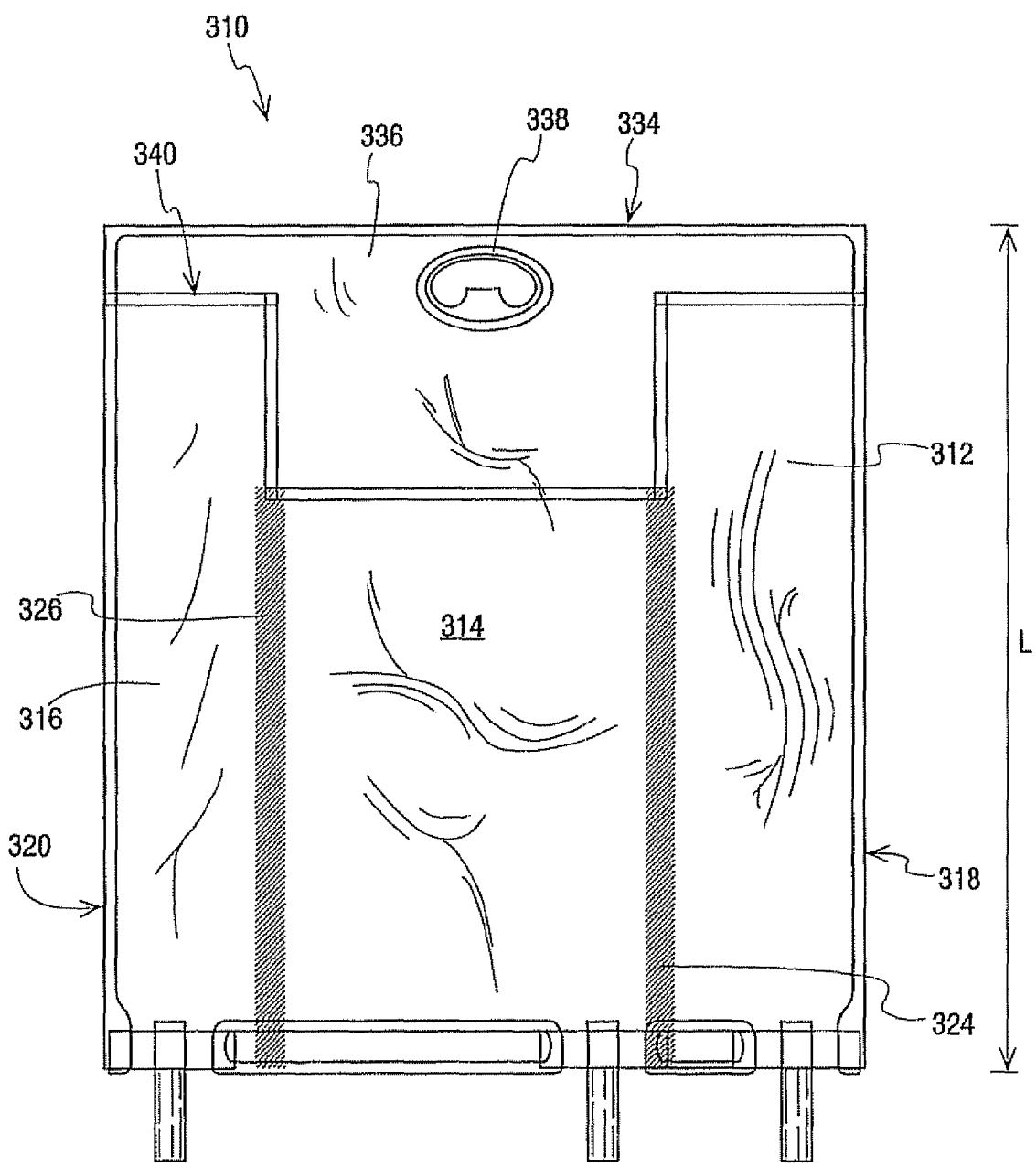
FIG. 7 is a plan view of another embodiment of a container of the present invention.
Figure 8:
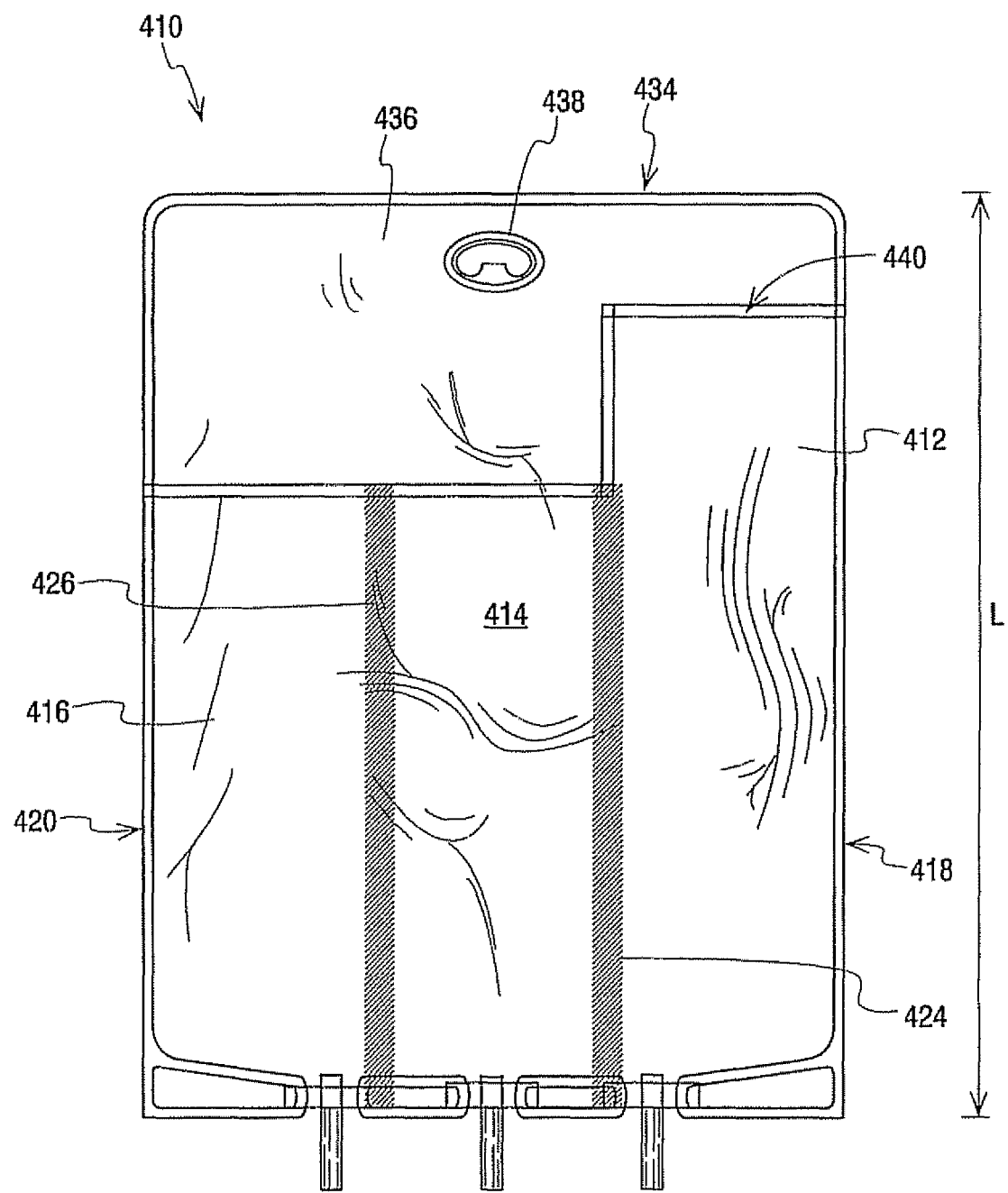
FIG. 8 is a plan view of another embodiment of a container of the present invention
Figure 9:
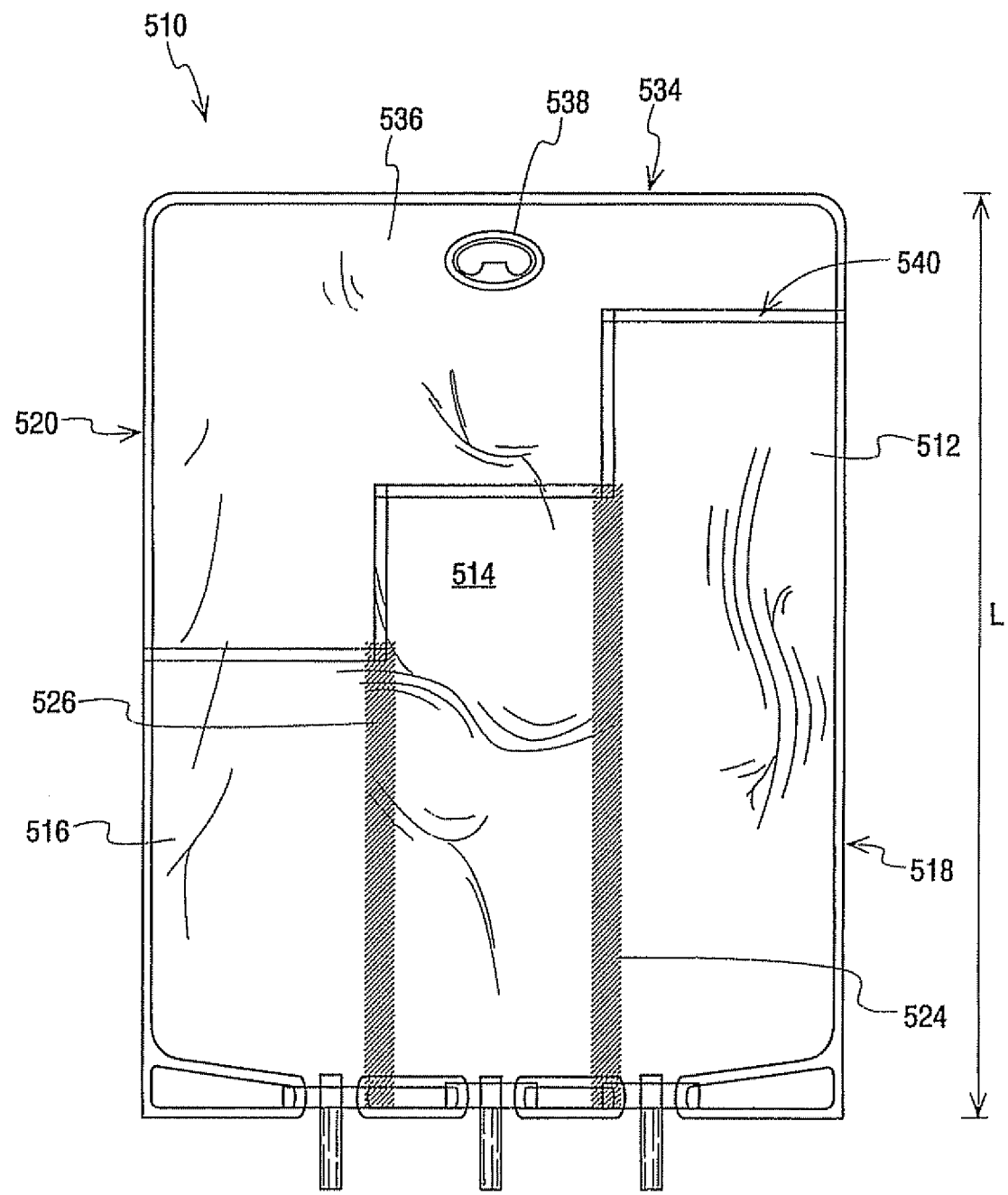
FIG. 9 is a plan view of another embodiment of a container of the present invention.

FIGS. 7, 8, and 9 illustrate other embodiments of a multiple chamber container of the present invention, Containers 310, 410, 510 all include three adjacent chambers 312, 314, 316 and 412, 414, 416, and 512, 514, 516, respectively. Chambers 312, 412, 512 are located at lateral or side ends 318, 418, 518, respectively and chambers 316, 416, 516 are located at opposite lateral or side ends 320, 420, 520. Hanger portion 336 is located at the top end 334 and includes hole 338 for hanging the container. Hanger portion 336 defines the top border 340 of chambers 312, 314, 316. Chambers 312 is separated from chamber 314 by peelable seal 324, and peelable seal 326 separates chamber 314 from 316. Container 410 also includes peelable seals 424, 426 separating chamber 412 from chamber 414 and chamber 414 from chamber 416, respectively.

Peelable seal 524 separates chamber 512 from chamber 514 and peelable seal 526 separates chamber 514 from 516. The peelable seals allow isolated storage of distinct formulations in the chambers for subsequent admixing prior to administration.

Chamber 314 has a longitudinal length that is from about two-thirds to about three-quarters the longitudinal lengths of both lateral end chambers 312, 316. While the longitudinal lengths of chambers 312, 316 are equal, differing lengths can be used, Selective activation of either peelable seal 324, 326 can occur when rolling container 310 starting at top end 334 and squeezing chamber 312 or chamber 316 depending on which of the peelable seals 324, 326 is to be activated.

As is shown in FIG. 8, the lateral end chamber 416 of container 410 has a longitudinal length that is from about two-thirds to about three-fourths less than the longitudinal length of chamber 412 positioned at opposite lateral end 418 and is equal to the longitudinal length of lateral end chamber 416. Chamber 412 having a longitudinal length greater than that of chamber 414 allows peelable seal 424 to be activated without the inadvertent activation of peelable seal 426 when rolling container 410 starting at top end 434.

Container 510 shown in FIG. 9 includes chambers 512, 514, 516 all of which have longitudinal lengths that differ from each other. Lateral end chamber 512 has a longitudinal length that is from about twenty five percent to about thirty three percent greater than the longitudinal length of chamber 514 which in turn has a longitudinal length that is from about twenty five percent to about thirty three percent greater than the longitudinal length of chamber 516. Rolling container 510 starting at the top end 534 allows selective activation of peelable seal 524, 526 by first pressurizing chamber 512 until seal 524 activates. Further rolling would begin to pressurized chamber 514 until seal 526 activates. Any additional chamber included between chamber 512 and 514 and having a longitudinal length less the longitudinal length of chamber 512 but greater than the longitudinal length of chamber 514, or between chamber 514 and 516 and having a longitudinal length less the longitudinal length of chamber 514 but greater than the longitudinal length of chamber 516 may allow sequential activation of seals starting with the seal bordering chamber 512 and end with the seal bordering chamber 516 when rolling the container, starting at the top end 534.

It is contemplated that one or more of the chambers could store a non-liquid such as a solid in powder or crystalline form with at least one chamber holding a liquid for dissolving the solid once the communication is established between the chambers.

Figure 10:
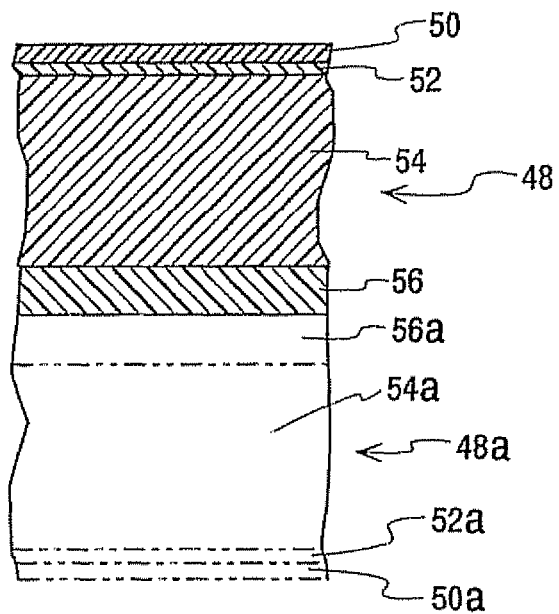
FIG. 10 is a plan view of another embodiment of a container of the present invention.

FIG. 10 is a cross-sectional view of one embodiment of the film or sheet 48 used to construct the container 10. Preferably, the sheet 48 is made from four layers 50, 52, 54 and 56. The outer layer 50 is preferably formed from a high melting temperature flexible material, more preferably a polyester material such as a poly-cyclohexane-di-methylcyclohexane-di-carboxylate elastomer ("PCCE") copolyester. Such a PCCE copolyester is sold by Eastman Kodak under the designation ECDEL® elastomer 9965, A typical thickness of the outer layer 50 is from about 0.39 mils to about 0.71 mils with the actual thickness of the outer layer show in FIG. 3 being 0.55 mils.

A tie layer 52 is provided to secure the first layer 50 to a third layer 54. Preferably the tie layer is a highly reactive polymer adhesive such as an ethylene vinyl acetate ("EVA") copolymer chemically modified with maleic acid. Such a material is available from DuPont under the name BYNEL ® plastic resin grade E-361, The tie layer 52 may have a varied thickness for example from 0.20 mils to 0-60 mils, e.g., 0.40 mils.

The third layer 54 preferably is a radio frequency (RE) responsive polymer, such as EVA copolymer. Such a material is available from DuPont under the name ELVAX® EVA resin 3182-2. Preferably the third layer has a thickness of about 5.56 mils to about 6.84 mils, e.g., 6.20 mils.

This film also includes a sealant layer 56 constructed of: 1) a bulk polyolefin that is thermally stable at heat sterilization temperatures, yet melts below the outside layer melting temperature; such polymers are preferably polypropylene-ethylene copolymers, such as grades Z9450 or 8650 from Total; and 2) a thermoplastic elastomer which produces a more flexible and free radical resistant sealant layer and gives the sealant layer two melt points with the elastomer having the lower value; such polymers preferably are styrene-ethylene-butene-styrene block copolymers such as KRATON® polymer G-1652 from Kraton polymers. The sealant layer preferably has a thickness of from about 1.28 mils to about 192 mils, e.g., 160 mils. The sealant layer 56 is adjacent the interior side of the container 10 (FIG. 1) such that when the seal is ruptured, communication is provided between the chambers.

The container 10 is constructed by overlaying two sheets on one another or by folding one sheet over onto itself or by flattening an extruded tube if tubular extrusion is used. FIG. 10 shows two sheets 48 and 48a with layer 56 contacting the corresponding layer 56a of sheet 48a. The sheets 48 and 48a are bonded or welded together permanently at the perimeter to form the container taking into account the placement of access ports. The sheets are also bonded together at other area to form the outer contours of the chamber that will be formed later. The heat seals are then formed to create the multiple chambers.

The peelable seals are formed preferably using a heated seal bar to heat and soften the layer 56, but not liquefy the layer. A resulting cohesive bond develops from contact between the sheet 48 and the sheet 48a, but fusion between the sheets, which can cause permanent bonding, does not occur. The peelable seals can be formed to require a force of from about 16 to about 21 Newtons to open or activate the peelable seals, preferably about 19 N. In order to obtain such an activation force, the temperature of the seal bar will vary depending upon the material used to construct the container. For film 48, the seal bar can be heated to from about 116 to about 122° C., preferably about 118° C. It should be noted that this temperature can vary substantially between different lots of the same film material and that the cohesive bond of the peelable seal is slightly reinforced or strengthened by heat sterilization.

A more detailed explanation of forming the peelable seal is provided in U.S. Pat. No. 6,319,243 which incorporated herein by reference.

Referring to FIG. 1, the ports 26, 28 and 30 can be constructed by any number of methods and by a variety of materials. Ports can be made from coextruded tube with clear PVC material inside to allow solvent-bonding to regular PVC closure systems. Alternatively, non-PVC tubes can be used. However, if one of the chambers is to contain a lipid for example in chamber 16 then port 30 is preferably constructed from a non-PVC containing material. If no administration site is added on the port of the chamber containing lipid, the port will be more preferably formed of a monolayer extruded tube with the following preferred formulation:

60% Polypropylene Total TOTAL® polymer 8473
40% Styrene ethylene butylenes styrene copolymer KRATON® polymer G1652

This port is then sealed off after filling.

If an administration site is added on the port of the chamber containing lipid, the port will be more preferably formed of a three layer coextruded tube with the following preferred formulations:

External layer (+/-330 um):
100% Polypropylene Solvay ELTEX® resin PKS490 or
[0076]
60% Polypropylene Total TOTAL® polymer 8473
40% Styrene ethylene butylenes styrene copolymer KRATON® polymer G1652
Medium layer (+/-170 um)
35% Polypropylene FORTILENE® polymer 4265
25% Polyethylene TAFMER® resin A4085
10% Styrene ethylene butylenes styrene copolymer KRATON® polymer F01924
10% Polyamide MACROMELT® resin TPXI6-159
20% EVA ESCORENE® resin UL00328) or
50% Styrene ethylene butylenes styrene copolymer KRATON® polymer G1660
38% Polyester Dupont HYTREL® thermoplastic resin 4056
10% EVA AT Plastic ATEVA® resin 2803G
2% Polypropylene Total TOTAL® polymer 6232
Internal layer (+/-330 um)
50% EVA ESCORENE® resin UL0019
50% EVA ESCORENE® resin UL00328 or
50% EVA ATEVA® resin 28030
50% EVA ATEVA® resin 1807G In a preferred embodiment some or all of the ports 22, 24, and 26 can be constructed from a non-PVC material such as the above formulation,

EXAMPLE 1

A comparison was of a 300 ml multi-chamber container of the present invention best exemplified by container 10 was compared to a currently available multi-chamber container which was the same in all respects to container 10 expect that the hanger flap extended only about half as far into the central chamber as hanger flap 36 extends into chamber 14 making the central chamber of this bag slightly larger in capacity. The same central and lateral end chambers were filled with water while the other lateral end chamber was filled with a colored solution, Additional water was added in the central chamber to compensate for the added volumetric capacity, In other words even though the central chamber of container 10 had a slightly smaller volume than the central chamber of other container they were similarly inflated with water.

Twenty operators were selected (10 male & 10 female). Each operator received 5 units of each design and the following instructions:

Instructions: For the ten containers, we are asking you to use the rolling procedure starting from the hanger end of the container to open only the peel seal separating the two compartments filled with colorless water. The peel seal separating the compartment filled with blue colored water should not be opened.

The operators were asked "Which design allows an easier and more efficient activation of only one peel seal of the bag?" All twenty selected container 10 of the present invention In different embodiment of the present invention, six parenteral nutritional (PN) formulations are provided for three patient populations. The patient populations are preterm infants (PT), term to two years old children (TT), and children over the age of two (OT). The PN formulation can have three components which are stored separately and mixed prior to administration. The three components can be a carbohydrate component, an amino acid (AA) component and a lipid component. One or more electrolytes can also preferably be included in the PN formulation. The electrolytes can be included in one or more of the components or can be added by the healthcare professional either before or after the components are combined. Preferably, one or more electrolytes can be included in the carbohydrate component, but more preferably, one or more of the electrolytes are included in the amino acid component.

The three components of the preterm PN formulation are preferably stored in a container having three chambers separated by openable seals such as frangible or peelable seals, having a total capacity of about 300 ml and having the ability to selectively open the seals, more preferably in container 10 (FIG. 1) described above. The three components of the PN formulation for term to two years old children is preferably stored in a similar three chamber container except that the container has a total capacity of about 500 ml, more preferably in container 110 (FIG. 5) described above. The three components of the PN formulation for children over the age of two are preferably stored in a similar three chamber container except that the container has a total capacity of about 1000 ml, more preferably in container 210 (FIG. 6) described above.

The carbohydrate component can include an aqueous solution containing from about 10% to about 70% of one or more carbohydrates such as glucose, fructose, and or sucrose. The amino acid component can include an aqueous solution containing from about 3% to about 10% of one or more amino acids. The lipid component can include an emulsion containing about 10% to about 30% of lipids such as fatty acids and/or triglycerides from plant, animal or synthetic sources such as, but not limited to olive oil, Medium Chain Triglyceride oil, soybean oil and fish oil. All of the percentages are expressed in weight to volume (w/v) unless otherwise specified.

Several members of the scientific community have determined mean nutritional recommended guidelines (MNRG) for the amino acids, carbohydrate, and lipid components and the likely minimum to maximum nutritional guidelines (MMNG) for the electrolytes see below per kilogram per day for the three patient populations as shown in the following table:

| NUTRIENT | PT (/kg/day) | TT (/kg/day) | OT (/kg/day) |
|---|---|---|---|
| Amino acid | 3.75 g | 2.5 g | 1.8 g |
| Carbohydrate | 16 g | 15 g | 15 g |
| Lipid | 3 g | 3 g | 2.2 g |
| Sodium | 0.0-2.5 mmol | 2.0-2.2 mmol | 1.0-3.5 mmol |
| Potassium | 0.0-2.5 mmol | 1.0-2.2 mmol | 1.0-2.5 mmol |
| Phosphorus | 1.0-2.25 mmol | 0.5-0.6 mmol | 0.2-0.6 mmol |
| Calcium* | 1.3-2.25 mmol | 0.5-0.6 mmol | 0.2-0.3 mmol |
| Magnesium | 0.2-0.5 mmol | 0.2-0.3 mmol | 0.1-0.2 mmol |
| Chloride | <6 mmol | 2-3 mmol | 3-5 mmol |
| Fluids (water) | 120 ml | 100 ml | 80 ml |

*The ratio of calcium to phosphorus should be between 1:1 and 1:1.1.

Referring to FIG. 1, in one embodiment of the present invention a PN formulation for preterm infants is provided in container 10. The PN formulation can include an amino acid component that can comprise a solution including water for injection, malic acid for pH adjustment to about 5.5 and the following amino acids:

| Amino Acid | Concentration (g/100 ml) |
|---|---|
| Lysine | 0.641 |
| Glutamic acid | 0.583 |
| Leucine | 0.583 |
| Arginine | 0.489 |
| Alanine | 0.466 |
| Valine | 0.443 |
| Isoleucine | 0.390 |
| Aspartic acid | 0.350 |
| Phenylalanine | 0.245 |
| Glycine | 0.233 |
| Serine | 0.233 |
| Histidine | 0.221 |
| Threonine | 0.216 |
| Ornithine (as 0.185 mg Ornithine Hydrochloride) | 0.145 |
| Proline | 0.175 |
| Methionine | 0.140 |
| Tryptophan | 0.117 |
| Cysteine | 0.110 |
| Taurine | 0.035 |
| Tyrosine | 0.045 |
| Totals | 5.726.860 |

While the above amino acids at their respective amounts are preferred, other amino acids in different amounts and combinations may be used. Nevertheless, cysteine should be present in amino acid solutions; specifically those administered to preterm infants because cysteine is a conditionally essential amino acid and because preterm infants a limited capacity to synthesize cysteine.

The PN formulation can also include a lipid component that can comprise a 12.5% lipid emulsion in water for injection

| Lipid emulsion at 12.5% | Role | Concentration |
|---|---|---|
| Purified olive oil | Active drug | about 80% of total oil |
| Soybean oil | Active drug | about 20% of total oil |
| Egg phospholipids | Emulsifier | 1.2% |
| Sodium oleate | Emulsifier | 0.03% |
| Glycerol | Iso-osmolarity | 2.25% |
| Water for injection | Dispersant | qs |

Olive oil is a preferred lipid because of its desirable immunoneutrality. The above combination is preferred because the combination evokes less peroxidation and no additional oxidative stress. While these are the preferred lipids and lipid concentration, other lipid sources may be used such as lipids from animal, vegetable or synthetic origin.

The PN can also include a carbohydrate component that can comprise a 50% aqueous glucose and electrolyte solution as shown in the following table:

| Nutrient | Source | Concentration (per 100 ml) |
|---|---|---|
| Na+ | Sodium Glycerophosphate | 3.4-7.8 mmol |
| P | Sodium Glycerophosphate | 1.7-3.9 mmol |
| Ca++ | Calcium Chloride | 2.7-4.7 mmol |
| K+ | Potassium Acetate | 0.0-7.8 mmol |
| Mg++ | Magnesium Acetate | 0.6-1.6 mmol |
| Cl– | Calcium Chloride | 5.4-9.4 mmol |
| Acetate– | Potassium Acetate and Magnesium Acetate | 0.6-9.4 mmol |
| Glucose | Glucose | 50.0 g |

Other sources and amounts for the electrolytes and carbohydrate may be used. It is preferred that the phosphorus comes from organic sources and the above table indicates the most preferred sources of the nutrients. It is also preferred that the pH be adjusted to about 4.0 and in the preferred embodiment the adjustment is achieved using hydrochloric acid along with other pH adjusters such as malic acid or ascetic acid to also achieve the desired level of chlorides.

Referring to FIG. 1, each chamber of container 10 is filled with one of the components of the PN formulation. In particular, containers of a PN formulation for pre-term infants may include about 80 ml of the carbohydrate component in chamber 12, about 160 ml of the amino acid component in chamber 14, and about 60 ml of the lipid component in chamber 16, In some instances it may not be advisable to administer the lipid component such as if it is the first day, the patient is suffering from septic shock, coagulation abnormalities, high bilirubin level or other reasons. In this case, container 10 permits the selective opening of seal 24.

In order to provide the MNRG (or nutrition at least at the minimum of MMNG) about 120 ml of the PN formulation should be infused per kilogram of the patient per day. The 300 ml container would then provide enough PN for 2.5 kg neonate (PT) over a 24-hour period. The following table illustrates the approximate values of the PN formulation in a three chambered container:

| Component | Amino Acid | Carbohydrate | Lipids | Total Volume |
|---|---|---|---|---|
| concentration (%) | 5.86 | 50 | 12.5 | — |
| ml/kg/day | 64 | 32 | 24 | 120 |
| ml/chamber | 160 | 80 | 60 | 300 |

In one embodiment, administration of about 120 ml/kg/day of the above PN formulation for preterm patients provides about the following nutrients and electrolytes:

| Nutrient/Electrolytes | Amount (/kg/day) |
|---|---|
| Na+ | 1.1-2.5 mmol |
| K+ | 0.0-2.5 mmol |
| P | 0.54-1.25 mmol |
| $P_{(Total)}$ (includes phosphorus present in lipid component) | 0.77-1.48 mmol |
| Ca++ | 0.9-1.5 mmol |

-continued

| Nutrient/Electrolytes | Amount (/kg/day) |
|---|---|
| Mg++ | 0.2-0.5 mmol |
| Cl- | 1.7-3.0 mmol |
| $Cl-_{(Total)}$ (includes chloride from amino acid Orn HCl) | 2.1-3.4 mmol |
| Acetate- | 0.2-3.0 mmol |
| Amino Acids | 3.75 grams |
| Glucose | 16 grams |
| Lipid | 3 grams |

It is desirable to provide calcium and phosphate levels above the lower end of the mean recommended requirements. However increasing the sodium glycerophosphate would cause the sodium level to exceed the upper range of the mean recommended requirement range. Although calcium can easily be increased by adding more calcium chloride, this would alter the recommended calcium to phosphorus ratio of 1:1 or 1:1.1. In one embodiment, an inorganic form of phosphorus is added to the amino acid component to meet the mean recommended requirement. In conjunction with this addition, more calcium is preferably added to maintain the proper ratio.

It may be desirable to provide less fluid than the mean recommended requirement so that other fluid therapy could be provided by the healthcare practitioner. Such fluid therapy is often necessary in patients that require PN. To allow the administration of other fluids, 120 ml/kg/day was chosen as being supplied in nutritional volume, while the overall required fluid level intake in preterm neonates is 150-170 ml/kg/day.

Referring to FIG. 5 in another embodiment of the present invention a PN formulation for term to two years old children is provided in a 500 ml container having three chambers preferably container 110. The PN formulation can include a carbohydrate component and can be housed in an end chamber 112 having a volumetric capacity of about 155 ml and having a longitudinal length substantially greater than the longitudinal length of the center chamber 114. This is to permit selective opening of the seal 124 adjacent the carbohydrate containing chamber 112 without opening the seal 122 adjacent chamber 116. An amino acid component can also be included in the PN formulation and can be housed in a central chamber 114 having a volumetric capacity of about 221 ml, Also, a lipid formulation can be included in the PN formulation and can be housed in an end chamber 116 having a volumetric capacity of about 124 ml. The lipid and amino acid components can be formulated as described above The carbohydrate component can comprise a 50% aqueous glucose and electrolyte solution as shown in the following table:

| Nutrient/ Electrolytes | Source | Concentration (per 100 ml) |
|---|---|---|
| Na+ | Sodium Glycerophosphate | 3.4-4.0 mmol |
| Na+ | Sodium Chloride | 0.0-3.3 mmol |
| K+ | Potassium Acetate | 3.3-7.3 mmol |
| P | Sodium Glycerophosphate | 1.7-2.0 mmol |
| Ca++ | Calcium Chloride | 0.8-2.0 mmol |
| Mg++ | Magnesium Acetate | 0.7-1.0 mmol |
| Cl- | Calcium Chloride and Sodium Chloride | 1.6-7.3 mmol |
| Acetate- | Potassium Acetate and Magnesium Acetate | 4.0-8.3 mmol |
| Glucose | Glucose | 50.0 g |

Other sources, amounts and combinations for the electrolytes and carbohydrate may be used. It is preferred that the phosphorus in the carbohydrate component comes from organic sources and the above table indicates the most preferred sources of the nutrients.

Each chamber is filled with one of the components. In particular, about 155 ml of the carbohydrate component can fill an end chamber 112 as described above, about 221 ml of the amino acid component can fill a central chamber 114 as described above, and about 124 ml of the lipid component can fill an end chamber 116 as described above. The above-described peel seal 124 allows mixing of the carbohydrate and amino acid components or all the seals 122, 124 may be opened to create the ternary PN formulation. So, in some instances where it may not be advisable to administer the lipid component such as if it is the first day of life, if the patient is suffering from septic shock, coagulation abnormalities, high bilirubin level or other reasons, the container permits the selective opening of only the seal adjacent an end chamber with the longitudinal length substantially greater than the longitudinal length of a central chamber without opening the seal adjacent the lipid chamber as discussed above.

In order to provide the MNRG and at least at the minimum of MMNG about 96.7 ml/kg/day of the PN formulation should be infused per kilogram of the patient per day. The 500 ml container would then provide enough PN for about a 5 kg child over a 24-hour period. The following table illustrates the approximate values of the PN formulation in a three chambered container:

| Component | Amino Acid | Carbohydrate | Lipids | Total Volume |
|---|---|---|---|---|
| concentration (%) | 5.86 | 50 | 12.5 | — |
| ml/kg/day | 42.7 | 30 | 24 | 96.7 |
| ml/chamber | 221 | 155 | 124 | 500 |

Administration of 96.7 ml/kg/day of the above PN formulation for term to two years old children provides approximately the following nutrients and electrolytes:

| Nutrient/Electrolytes | Amount (per kg/day) |
|---|---|
| Na+ | 1.0-2.2 mmol |
| K+ | 1.0-2.2 mmol |
| P | 0.5-0.6 mmol |
| $P_{(Total)}$ (includes phosphorus present in lipid component) | 0.73-0.83 mmol |
| Ca++ | 0.24-0.60 mmol |
| Mg++ | 0.2-0.3 mmol |
| Cl- | 0.5-2.2 mmol |
| $Cl-_{(Total)}$ (includes chloride from amino acid Orn HCl) | 0.7-2.4 mmol |
| Acetate- | 1.2-2.5 mmol |
| Amino Acids | 2.5 grams |
| Glucose | 15 grams |
| Lipid | 3 grams |

With all lipids added, phosphorus intake is higher and the P/Ca ratio increases, however, this patient population can accommodate such a small excess of phosphorus. The reduced fluid amount permits the healthcare professional to administer other fluid therapy if necessary which may be advantageous in certain circumstances.

Referring to FIG. 6, in another embodiment of the present invention, a PN formulation for children over the age of two is provided in a 1000 ml container having three chambers, preferably container 210. The PN formulation can include a carbohydrate component and can be housed in an end chamber 212 having a volumetric capacity of about 383 ml and having a longitudinal length substantially greater than the longitudinal length of the center chamber 214, This is to permit selective opening of the seal 224 adjacent the carbohydrate containing chamber 212 without opening the seal 222 adjacent chamber 216. An amino acid component can be included in the PN formulation and can be housed in central chamber 214 having a volumetric capacity of about 392 ml. In addition, a lipid component can be included in the PN formulation and can be housed in an end chamber 216 having a volumetric capacity of about 225 ml. The lipid and amino acid components can be formulated as described above. The carbohydrate component can comprise a 50% aqueous glucose and electrolyte solution as shown in the following table

| Nutrient/Electrolytes | Source | Concentration (per 100 ml) |
|---|---|---|
| Na+ | Sodium Glycerophosphate | 1.0-3.7 mmol |
| Na+ | Sodium Chloride | 2.2-8.0 mmol |
| K+ | Potassium Acetate | 3.3-8.3 mmol |
| P | Sodium Glycerophosphate | 0.65-1.83 mmol |
| Ca++ | Calcium Chloride | 0.65-1.00 mmol |
| Mg++ | Magnesium Acetate | 0.33-0.67 mmol |
| Cl− | Calcium Chloride, Sodium Chloride | 3.5-10.0 mmol |
| Acetate− | Potassium Acetate and Magnesium Acetate | 3.6-9.0 mmol |
| Glucose | Glucose | 50.0 g |

Other sources, amounts and combinations for the electrolytes and carbohydrate may be used. It is preferred that the phosphorus in the carbohydrate component come from organic sources and the above table indicates the most preferred sources of the nutrients.

Each chamber is filled with one of the components. In particular, about 383 ml of the carbohydrate component fills end chamber 212 as described above, about 392 ml of the amino acid component fills central chamber 214 as described above, and about 225 ml of the lipid component fills end chamber 216 as described above. Each component can be administered to the patient separately or all the seals 222, 224 may be opened to create the PN formulation. However, in some instances it may not be advisable to administer the lipid component such as if it is the first day, the patient is suffering from septic shock, coagulation abnormalities, high bilirubin level or other reasons. In this case, the container permits the selective opening of the seal adjacent an end chamber having a longitudinal length substantially greater the longitudinal length of the central chamber without opening the seal adjacent the lipid chamber as discussed above.

In order to provide the MNRG and at least at the minimum of MMNG), about 78.3 ml/kg/day of the PN formulation should be infused per kilogram of the patient per day. The 1000 ml container would then provide enough PN for about a 12.5 kg child over a 24-hour period. The following table illustrates the approximate values of the PN formulation in a three chambered container:

| Component | Amino Acid | Carbohydrate | Lipids | Total Volume |
|---|---|---|---|---|
| concentration (%) | 5.86 | 50 | 12.5 | — |
| ml/kg/day | 30.7 | 30 | 17.6 | 78.3 |
| ml/chamber | 392 | 383 | 225 | 1000 |

Administration of about 78.3 ml/kg/day of the above PN formulation for children over the age of two provides about the following nutrients and electrolytes:

| Nutrient/Electrolytes | Amount (per kg/day) |
|---|---|
| Na+ | 1.0-3.5 mmol |
| K+ | 1.0-2.5 mmol |
| P | 0.20-0.55 mmol |
| $P_{(Total)}$ (includes phosphorus present in lipid component) | 0.37-0.72 mmol |
| Ca++ | 0.2-0.3 mmol |
| Mg++ | 0.1-0.2 mmol |
| Cl− | 1.0-3.0 mmol |
| $Cl-_{(Total)}$ (includes chloride from amino acid Orn HCl) | 1.1-3.1 mmol |
| Acetate− | 1.1-2.7 mmol |
| Amino Acids | 1.8 grams |
| Glucose | 15 grams |
| Lipid | 2.2 grams |

The reduced fluid level permits the healthcare professional to administer other fluid therapy which may be desirable in certain circumstances In another embodiment of the present invention, a PN formulation for children over the age of two is provided in a 1000 ml container having three chambers, preferably container 210. The PN formulation can include a carbohydrate component and can be housed in an end chamber 212 having a volumetric capacity of about 332 ml and having a longitudinal length substantially greater than the longitudinal length of central chamber 214. This is to permit selective opening of the seal 224 adjacent the carbohydrate containing chamber 212 and without opening the seal 222 adjacent chamber 216. An amino acid component can also be included in the PN formulation and can be housed in a central chamber 214 having a volumetric capacity of about 425 ml. A lipid component can also be included in the PN formulation and can be housed in an end chamber 216 having a volumetric capacity of about 243 ml. The lipid and amino acid components are formulated as described above. In the preferred embodiment the carbohydrate component comprises a 62.5% aqueous glucose and electrolyte solution as shown in the following table

| Nutrient/Electrolytes | Source | Concentration (per 100 ml) |
|---|---|---|
| Na+ | Sodium Glycerophosphate | 1.285-4.583 mmol |
| Na+ | Sodium Chloride | 2.804-9.998 mmol |
| K+ | Potassium Acetate | 4.09-10.415 mmol |
| P | Sodium Glycerophosphate | 0.818-2.291 mmol |
| Ca++ | Calcium Chloride | 0.818-1.250 mmol |
| Mg++ | Magnesium Chloride | 0.409-0.833 mmol |
| Cl− | Calcium Chloride, Sodium Chloride and Magnesium Chloride | 14.643 mmol |
| Glucose | Glucose | 62.5 g |

Other sources, amounts and combinations for the electrolytes and carbohydrate may be used. It is preferred that the phosphorus in the carbohydrate component come from organic sources and the above table indicates the most preferred sources of the nutrients.

Each chamber is filled with one of the components. In particular, about 332 ml of the carbohydrate component fills an end chamber 212 as described above, about 425 ml of the amino acid component fills a central chamber 214 as described above, and about 243 ml of the lipid component fills an end chamber 216 as described above. Each component can be administered to the patient separately or all the seals 222, 224 may be opened to create the PN formulation. However, in some instances it may not be advisable to administer the lipid component such as if the patient is suffering from septic shock, coagulation abnormalities, high bilirubin level or other reasons. In this case, the container permits the selective opening of the seal 224 adjacent an end chamber 212 having a longitudinal length substantially greater than the longitudinal length of the central chamber 214 without opening the seal 222 adjacent the lipid compartment 216 as discussed above.

In order to provide the MNRG and at least at the minimum of MMNG, about 72.3 ml/kg/day of the described PN formulation should be infused per kilogram of the patient per day. The 1000 ml container provides enough PN per day for about a 13.5 kg child over a 24-hour period. Thus this container provides for a larger child over a 24 hour period than the previously described embodiment of a 1000 ml chamber. The following table illustrates the approximate values of the PN formulation in a three chambered container:

| Component | Amino Acid | Carbohydrate | Lipids | Total Volume |
|---|---|---|---|---|
| concentration (%) | 5.86 | 62.5 | 12.5 | — |
| ml/kg/day | 30.7 | 30 | 17.6 | 72.3 |
| ml/chamber | 425 | 332 | 243 | 1000 |

Administration of about 72.3 ml/kg/day of the above PN formulation for children over the age of two provides the following nutrients and electrolytes:

| Nutrient/Electrolytes | Amount (/kg/day) |
|---|---|
| Na+ (includes sodium glycerophosphate and sodium chloride) | 1.0-3.5 mmol |
| K+ | 1.0-2.5 mmol |
| P | 0.2-0.55 mmol |
| $P_{(Total)}$ (includes phosphorus present in lipid component) | 0.2-0.715 mmol |
| Ca++ | 0.2-0.3 mmol |
| Mg++ | 0.1-0.2 mmol |
| Cl− (Magnesium chloride, calcium chloride and sodium chloride) | 3.4 mmol |
| $Cl-_{(Total)}$ (includes chloride from amino acid Orn HCl) | 3.51 mmol |
| Amino Acids | 1.8 grams |
| Glucose | 15 grams |
| Lipid | 2.2 grams |

The reduced fluid level permits the healthcare professional to administer other fluid therapy which may be desirable in certain circumstances.

In some instances it has been determined that any increase in the electrolyte concentration above the minimum level increases the buffer capacity of the carbohydrate component (aqueous glucose and electrolyte solution). This increased buffer capacity results in the lowering of the pH of the admixed PN formulation to a level potentially incompatible with the targeted pediatric populations.

As a result, it may be preferable to either not include electrolytes beyond the minimum concentration shown above, to not include electrolytes beyond the minimum concentration shown above in the PN formulation as manufactured but allowing the addition of electrolytes by the healthcare practitioner prior, to administration) or to include the electrolytes even at concentrations above the minimum base level in another component.

Therefore in these instances, in more preferred embodiments of the present invention, three parenteral nutritional (PN) formulations are provided for the above described patient populations, i.e. pre-term infants (PT), term to two years old children (TT), and children over the age of two (OT). The more preferred PN formulation can have three components which are stored separately and mixed prior to administration. The three components can be a carbohydrate component, an amino acid (AA) component and a lipid component. One or more electrolytes can also preferably be included in the PN formulation, more preferably a number of electrolytes are included in the amino acid component The three components of the preterm PN formulation are preferably stored in a container having three chambers separated by openable seals such as frangible or peelable seals, having a total capacity of about 300 ml and having the ability to selectively open the seals, more preferably in container 10 (FIG. 1) described above. The three components of the PN formulation for term to two years old children are preferably stored in a similar three chamber container except that the container has a total capacity of 500 ml, mole preferably in container 110 (FIG. 5) described above. The three components of the PN formulation for children over the age of two are preferably stored in a similar three chamber container except that the container has a total capacity of 1000 ml, more preferably in container 210 (FIG. 6) described above.

The carbohydrate component can include an aqueous solution containing from about 10% to about 70% of one or more carbohydrates such as glucose, fructose and/or sucrose. The amino acid component can include an aqueous solution containing from about 3% to about 10% of one or more amino acids. The lipid component can include an emulsion containing about 10% to about 30% of lipids such as fatty acids and/or triglycerides from plant, animal or synthetic sources such as, but not limited to olive oil, Medium Chain Triglyceride oil, soybean oil and fish oil. All of the percentages are expressed in weight to volume (w/v) unless otherwise specified.

A preferred lipid component for the PN formulation for all three patient populations (PT, TT and OT) comprise a 12.5% lipid emulsion in water for injection as described previously.

Olive oil is a preferred lipid because of its desirable immunoneutrality. The above combination is preferred because the combination evokes less peroxidation and no additional oxidative stress. While these are the preferred lipids and lipid concentration, other lipid sources may be used such as lipids from animal, vegetable or synthetic origin.

A preferred carbohydrate component for the PN formulation for all three patient populations (PT, TT and OT) can comprise 50.0% glucose in water for injection. One or more carbohydrates may be used in lieu of glucose. The pH should be adjusted to about 4.0 and in a preferred embodiment the adjustment may be accomplished with hydrochloric acid.

A preferred amino acid component for the PN formulation for each of the three patient populations (PT, TT and OT) can comprise a solution of amino acids and electrolytes. The approximate amounts of the constituents of the amino acid component for each patient population are shown in the following table A:

| Compound | Patient Population PT | Patient Population TT | Patient Population OT |
|---|---|---|---|
| Alanine | 0.466 g | 0.466 g | 0.466 g |
| Arginine | 0.489 g | 0.489 g | 0.489 g |
| Aspartic acid | 0.350 g | 0.350 g | 0.350 g |
| Cysteine | 0.110 g | 0.110 g | 0.110 g |
| Glutamic acid | 0.583 g | 0.583 g | 0.583 g |
| Glycine | 0.233 g | 0.233 g | 0.233 g |
| Histidine | 0.221 g | 0.221 g | 0.221 g |
| L-Isoleucine | 0.390 g | 0.390 g | 0.390 g |
| Leucine | 0.583 g | 0.583 g | 0.583 g |
| Lysine | 0.644 g | 0.644 g | 0.644 g |
| Methionine | 0.140 g | 0.140 g | 0.140 g |
| Ornithine | 0.145 g | 0.145 g | 0.145 g |
| (as L-Ornithine hydrochloride) | (0.185 g) | (0.185 g) | (0.185 g) |
| Phenylalanine | 0.245 g | 0.245 g | 0.245 g |
| Proline | 0.175 g | 0.175 g | 0.175 g |
| Serine | 0.233 g | 0.233 g | 0.233 g |
| Taurine | 0.035 g | 0.035 g | 0.035 g |
| Threonine | 0.216 g | 0.216 g | 0.216 g |
| Tryptophane | 0.117 g | 0.117 g | 0.117 g |
| Tyrosine | 0.045 g | 0.045 g | 0.045 g |
| Valine | 0.443 g | 0.443 g | 0.443 g |
| Sodium (source(s) can include sodium glycerophosphate and/or sodium chloride) | 3.9 mmol | 5.1 mmol | 11.4 mmol |
| Potassium (source(s) can include potassium acetate) | 3.9 mmol | 5.1 mmol | 8.2 mmol |
| Magnesium (source(s) can include magnesium acetate) | 0.78 mmol | 0.70 mmol | 0.65 mmol |
| Calcium (source(s) can include calcium chloride) | 2.35 mmol | 1.40 mmol | 0.98 mmol |
| Phosphate | 2.0 mmol | 1.45 mmol | 1.85 mmol |
| Acetate (the amount of acetate my vary depending on the source of the other electrolytes) | 4.7 mmol appr. | 5.9 mmol appr. | 8.8 mmol appr. |
| Malate | 1.9 mmol | 1.9 mmol | 2.0 mmol |
| Chloride (the amount of chloride my vary depending on the source of the other electrolytes) | 5.8 mmol appr. | 6.2 mmol appr. | 11.0 mmol appr. |
| Malic acid | qs to pH 5.5 | qs to pH 5.5 | qs to pH 5.5 |
| Water for injection | qs to 100 ml | qs to 100 ml | qs to 100 ml |

Other sources, combinations and amounts for the electrolytes and amino acids may be used. It is preferred that the phosphorus comes from organic sources and the above table indicates the most preferred sources of the nutrients.

Referring to FIG. 1, each chamber of container 10 is filled with one of the components of the PN formulation. In particular, containers of a PN formulation for pre-term infants may include about 80 ml of the carbohydrate component in chamber 12, about 160 ml of the amino acid component for the PT population in chamber 14, and about 60 ml of the lipid component in chamber 16. In some instances it may not be advisable to administer the lipid component such as if it is the first day, the patient is suffering from septic shock, coagulation abnormalities, high bilirubin level or other reasons. In this case, container 10 permits the selective opening of the seals.

In order to provide the MNRG for the amino acids, carbohydrate, lipid and electrolytes about 120 ml of the PN formulation should be infused per kilogram of the patient per day. The 300 ml container would then provide enough PN for 2.5 kg neonate (PT) over a 24-hour period. The following table illustrates the approximate values of the PN formulation in a three chambered container.

| Component | Amino Acid | Carbohydrate | Lipids | Total Volume |
|---|---|---|---|---|
| concentration (%) | 5.86 | 50 | 12.5 | — |
| ml/kg/day | 64 | 32 | 24 | 120 |
| ml/chamber | 160 | 80 | 60 | 300 |

In one embodiment, administration of about 120 ml/kg/day of the above PN formulation for preterm patients provides about the following nutrients and electrolytes:

| Nutrient/Electrolytes | Amount (/kg/day) |
|---|---|
| Na+ | 2.6 mmol |
| K+ | 2.5 mmol |
| P | 1.3 mmol |
| $P_{(Total)}$ (includes phosphorus present in lipid component) | 1.5 mmol |
| Ca++ | 1.5 mmol |
| Mg++ | 0.5 mmol |
| Cl− | 3.7 mmol |
| Acetate− | 3.0 mmol |
| Amino Acids | 3.75 grams |
| Glucose | 16 grams |
| Lipid | 3 grams |

It is desirable to provide calcium and potassium levels above the lower end of the mean recommended requirements. However increasing the sodium glycerophosphate would cause the sodium level to exceed the upper range of the mean recommended requirement range. Although calcium can easily be increased by adding more calcium chloride, this would alter the recommended calcium to phosphorus ratio of 1:1 or 1:1.1. In one embodiment, an inorganic form of phosphorus is added to the amino acid component to meet the mean recommended requirement. In conjunction with this addition, more calcium is preferably added to maintain the proper ratio.

It may be desirable to provide less fluid than the mean recommended requirement so that other fluid therapy could be provided by the healthcare practitioner. Such fluid therapy is often necessary in patients that require PN. To allow the administration of other fluids, 120 ml/kg/day was chosen as being supplied in nutritional volume, while the overall required fluid level intake in preterm neonates is 150-170 ml/kg/day.

Referring to FIG. 5 in another embodiment of the present invention a PN formulation for term to two years old children is provided in a 500 ml container having three chambers, preferably container 110. The PN formulation can include a carbohydrate component and can be housed in an end chamber 112 having a volumetric capacity of about 155 ml and having a longitudinal length substantially greater than the longitudinal length of the center chamber 114. This is to permit selective opening of the seal 124 adjacent the carbohydrate containing chamber 112 without opening the seal 122 adjacent chamber 116. An amino acid component can also be included in the PN formulation and can be housed in a central chamber 114 having a volumetric capacity of about 221 ml. Also, a lipid formulation can be included in the PN formulation and can be housed in an end chamber 116 having a volumetric capacity of about 124 ml.

The lipid component can be formulated as described above and the amino acid component can be formulated for the TT population as shown in table A above.

A preferred carbohydrate component for the PN formulation for all three patient populations (PT, TT and OT) can comprise 50.0% glucose in water for injection. One or more carbohydrates may be used in lieu of glucose. In the preferred embodiment the pH may be adjusted to around 4.0 with hydrochloric acid.

Each chamber is filled with one of the components. In particular, about 155 ml of the carbohydrate component can fill an end chamber 112 as described above, about 221 ml of the amino acid component can fill a central chamber 114 as described above, and about 124 ml of the lipid component can fill an end chamber 116 as described above. The above-described optional peel seal 124 allows to mix the carbohydrate and amino acid components or all the seals 122, 124 may be opened to create the ternary PN formulation. So, in some instances where it may not be advisable to administer the lipid component such as if it is the first day of life, if the patient is suffering from septic shock, coagulation abnormalities, high bilirubin level or other reasons, the container permits the selective opening of only the seal adjacent an end chamber with the longitudinal length substantially greater than the longitudinal length of a central chamber without opening the seal adjacent the lipid chamber as discussed above.

In order to provide the MNRG for the amino acids, carbohydrate, lipid and electrolytes about 96.7 ml/kg/day of the PN formulation should be infused per kilogram of the patient per day. The 500 ml container would then provide enough PN for about a 5 kg child over a 24-hour period. The following table illustrates the approximate values of the PN formulation in a three chambered container:

| Component | Amino Acid | Carbohydrate | Lipids | Total Volume |
| --- | --- | --- | --- | --- |
| concentration (%) | 5.86 | 50 | 12.5 | — |
| ml/kg/day | 42.7 | 30.0 | 24 | 96.7 |
| ml/chamber | 221 | 155 | 124 | 500 |

Administration of 96.7 of the above PN formulation for term to two years old children provides approximately the following nutrients and electrolytes:

| Nutrient/Electrolytes | Amount (per kg/day) | |
| --- | --- | --- |
| Na+ | 2.3 | mmol |
| K+ | 2.2 | mmol |
| P | 0.62 | mmol |
| $P_{(Total)}$ (includes phosphorus present in lipid component) | 0.84 | mmol |
| Ca++ | 0.60 | mmol |
| Mg++ | 0.30 | mmol |
| Cl– | 2.7 | mmol |
| Acetate– | 2.5 | mmol |
| Amino Acids | 2.5 | grams |
| Glucose | 15 | grams |
| Lipid | 3 | grams |

With all lipids added, phosphorus intake is higher and the P/Ca ratio increases, however, this patient population can accommodate such a small excess of phosphorus. The reduced fluid amount permits the healthcare professional to administer other fluid therapy if necessary which may be advantageous in certain circumstances. Referring to FIG. 6, in another embodiment of the present invention, a PN formulation for children over the age of two is provided in a 1000 ml container having three chambers, preferably container 210. The PN formulation can include a carbohydrate component and can be housed in an end chamber 212 having a volumetric capacity of about 383 ml and having a longitudinal length substantially greater than the longitudinal length of the center chamber 214. This is to permit selective opening of the seal 224 adjacent the carbohydrate containing chamber 212 without opening the seal 222 adjacent chamber 216. An amino acid component can be included in the PN formulation and can be housed in central chamber 214 having a volumetric capacity of about 392 ml. In addition, a lipid component can be included in the PN formulation and can be housed in an end chamber 216 having a volumetric capacity of about 225 ml.

The lipid component can be formulated as described above and the amino acid component can be formulated for the TT population as shown in table A above.

A preferred carbohydrate component for the PN formulation for all three patient populations (PT, TT and OT) can comprise 50.0% glucose in water for injection. One or more carbohydrates may be used in lieu of glucose. In the preferred embodiment the pH may be adjusted to around 4.0 with hydrochloric acid.

Each chamber is filled with one of the components. In particular, about 383 ml of the carbohydrate component fills end chamber 212 as described above, about 392 ml of the amino acid component fills central chamber 214 as described above, and about 225 ml of the lipid component fills end chamber 216 as described above. Each component can be administered to the patient separately or all the seals 222, 224 may be opened to create the PN formulation. However, in some instances it may not be advisable to administer the lipid component such as if it is the first day, the patient is suffering from septic shock, coagulation abnormalities, high bilirubin level or other reasons. In this case, the container permits the selective opening of only the seal adjacent an end chamber with having a longitudinal length substantially greater the longitudinal length of the central chamber without opening the seal adjacent the lipid chamber as discussed above.

In order to provide the MNRG for the amino acids, carbohydrate, lipid and electrolytes, about 78.3 ml/kg/day of the PN formulation should be infused per kilogram of the patient per day. The 1000 ml container would then provide enough PN for about a 12.5 kg child over a 24-hour period. The following table illustrates the approximate values of the PN formulation in a three chambered:

| Component | Amino Acid | Carbohydrate | Lipids | Total Volume |
| --- | --- | --- | --- | --- |
| concentration (%) | 5.86 | 50 | 12.5 | — |
| ml/kg/day | 30.7 | 30 | 17.6 | 78.3 |
| ml/chamber | 392 | 383 | 225 | 1000 |

Administration of about 78.3 ml/kg/day of the above PN formulation for children over the age of two provides about the following nutrients and electrolytes:

| Nutrient/Electrolytes | Amount (per kg/day) | |
| --- | --- | --- |
| Na+ | 3.6 | mmol |
| K+ | 2.5 | mmol |

-continued

| Nutrient/Electrolytes | Amount (per kg/day) |
|---|---|
| P | 0.57 mmol |
| $P_{(Total)}$ (includes phosphorus present in lipid component) | 0.73 mmol |
| Ca++ | 0.30 mmol |
| Mg++ | 0.20 mmol |
| Cl− | 3.4 mmol |
| Amino Acids | 1.8 grams |
| Glucose | 15 grams |
| Lipid | 2.2 grams |

The reduced fluid level permits the healthcare professional to administer other fluid therapy which may be desirable in certain circumstances.

Figure 11:
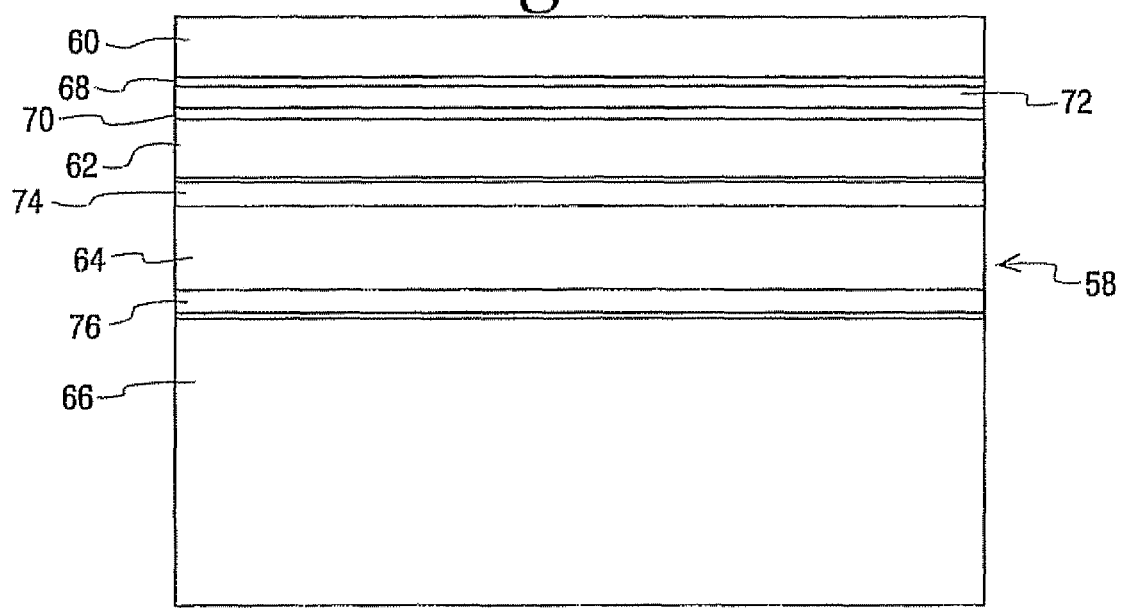
FIG. 11 is a cross sectional view of one embodiment of a flexible film material used to construct the overpouch of the present invention.

Referring to FIG. 11, containers of TPN formulations in accordance with the present invention may be placed in pouches selected to retain solution viability and protect the solution from degradation. In one embodiment of the present invention, an overpouch is provided for housing a container 10, 110, 210, 310, 410, 510 having multiple chambers containing a carbohydrate component, a lipid component and an amino acid component of a TPN formulation. The overpouch is preferably constructed of a multi-layered plastic film of sheet and prevents oxygen from entering the interior of the overpouch. It is also preferable that the overpouch is able to withstand sterilization such as autoclaving.

One or more of the layers of the film used to construct the overpouch can include oxygen scavenging polymers or the layer can provide a physical barrier to prevent oxygen permeation.

FIG. 11 shows a cross-section of one embodiment of the film 3-1-0 58 used to construct the overpouch. The preferred film 58 comprises 4 layers 60, 62, 64, and 66. Layer 60 is the exterior most layer of the film and is preferably a high melting temperature polymer having an oxygen barrier coating, As illustrated, layer 60 is a polyester material having an aluminum oxide coating 68. The thickness of layer 60 can range from about 6 to about 18 um, preferably from about 10 to about 14 um, most preferably about 12 um. The coating 68 can have a thickness of about 400 Angstrom. The layer 60 is oriented so that the aluminum oxide coating faces toward the interior of the overpouch.

Preferably, the next layer 62 moving towards the interior is same as layer 60 except that the coating 70 faces the exterior. A different polymer having oxygen impermeable qualities can be used instead such as an oxygen scavenging polymer.

The two layers 60 and 62 are bonded or welded together in a variety of ways. As shown on FIG. 111, an adhesive 72 is placed between layers 60 and 62. The adhesive can be applied in a thickness range of from about 1.5 to about 5.5 um, preferably about 3.5 um, While many different adhesive may be used, the preferred adhesive is a polyurethane-polyester resin adhesive.

Layer 64 is preferably a nylon material, more preferably nylon-6. The thickness of layer 64 can be from about 10 to about 20 um, with the preferred thickness being about 15 um. Layer 64 is bonded to layer 62 with adhesive 74 which in this embodiment is the same adhesive and thickness as adhesive 72.

Layer 66 is the interior most layer and is preferably a polypropylene material, more preferably a cast polypropylene The thickness of layer 66 can range from about 30 to about 70 um, more preferably about 50 um.

Layers 64 and 66 are also bonded together with an adhesive 76 which in this embodiment is the same adhesive and having the same thickness as adhesive 72.

In another embodiment, the overpouch can be made from two webs having different structures. The top web can be the structure described above whereas the bottom web could be a thermoformable structure or an opaque structure or could have a sealant layer allowing peelable opening.

A multiple chamber container 10 (FIG. 1) storing a TPN formulation is then placed in the overpouch. Preferably the headspace of the overpouch is filed with an inert gas such as nitrogen to remove the atmospheric oxygen and then the overpouch can be sealed. The overpouch can be closed using an adhesive or by heat sealing. Once the overpouch is seal shut the entire package can be sterilized.

It is known that heat sterilization of amino acid solutions having amino acids with a thiol function such as cysteine or N-acetyl-cysteine can produce hydrogen sulfide gas as a decomposition product and most likely also ppb levels of other unidentified volatile organic sulphured compounds noticeable by their odor. Hydrogen sulfide equilibrates between the liquid phase and the gaseous phase or headspace if present. A limit of 1 ppm of hydrogen sulfide in the aqueous phase has been assessed as non-toxic for the patient by intravenous route. But even if this limit in the aqueous phase is applied, some hydrogen sulfide and related sulphured compounds in the gaseous phase can still be present at a very low level but at a level sufficient to produce an unpleasant odor, (hydrogen sulfide can be smelled from levels of 0.1 ppm in the gaseous phase). This unpleasant odor can be disconcerting to the patient and others in the area and create an impression that the TPN formulation is stale or contaminated.

In this regard, to remove any unpleasant odor linked to very low levels of hydrogen sulfide and/or related sulphured compounds in the gaseous phase, before the overpouch is sealed shut a odor absorber (not shown) can be placed in the overpouch. There are many types of absorbers that can be used and most of them contain active carbon that attracts and attaches the molecules to the surface of the pores with Van der Waals forces mechanism. In addition, an oxygen absorber can also be placed in the overpouch to absorb any oxygen that may still be left inside the over pouch or that may diffuse through the overpouch material during the shelf life of the product. The oxygen absorber has also the capability to absorb the $H_2S$ by establishing covalent bonding with iron to form iron sulfur. It is also contemplated that a combined oxygen and odor scavenger may be used.

It should be noted that the container housing the cysteine containing TPN formulation should be permeable to the hydrogen sulfide so that it can enter the interior of the overpouch were it can be absorbed or scavenged.

In a further embodiment of the present invention, sterilization at a slightly higher temperature than the industry standard of 121 degrees centigrade may be performed to reduce the level of hydrogen sulfide. For example, sterilization at 125 degrees centigrade and for a shorter time period or sterilization cycle has been found to reduce hydrogen sulfide levels and reduce the degradation of some of the amino acids. With less degradation the formulated levels of amino acids can be closer to the levels desired after sterilization which facilitates the ability to tightly control the amino acid levels.

In another embodiment of the present invention an oxygen indicator is provided Oxygen indicators are used to demonstrate that the oxygen sensitive components of TPN formulation such as lipid emulsions were not exposed to undesired oxygen levels during transport and/or storage. A preferred oxygen indicator provides a distinct and marked color change to indicate oxygen is present even after undergoing heat sterilization. Moreover, once the color change has occurred the oxidized color must then remain substantially unchanged visually to the observer in circumstances in which the indicator is not observed for some time such as during prolonged storage.

In an embodiment of an indicator the indicator of the present invention is placed in the overpouch and may be adhered to the medical container prior to sterilization. Thus the indicator must be able to withstand steam sterilization. In other words the reduced color of the indicator, i.e. the color of the indicator prior to exposure to oxygen sufficient to oxidize the indicator, should still change color when oxidized (exposed to a sufficient amount of oxygen) and the oxidized color should remain substantially unchanged visually and distinct from the reduced color. In a preferred embodiment, the indicator is manufactured in its oxidized form and is reduced upon steam sterilization. Additionally, both the color of the reduced form and the color of the oxidized form should not fade or significantly change during storage of up to three months at 40° C. more preferably up to six months at 40° C. Further, both the color of the reduced form and the color of the oxidized form should not fade or significantly change during storage of up to two years at 25° C. and 30° C.

Typically the oxygen indicators come in small pouches containing an indicator solution. The pouches are usually constructed of a top web and bottom or base web which awe scaled about their edges to each other to create a sealed pouch. An adhesive such as double-side tape can be placed on the base web to fix the indicator pouch inside the secondary packaging or to the container housing the medical formulation. In a preferred embodiment, the indicator is fixed on the surface of the oxygen absorber. The material forming the pouch can be selected to comply with the kinetic of color change requirement Some such materials can be:

top web: Oriented polypropylene (OPP) 25μ/Cast polypropylene (CCP) 40μ. A multi color printing can be applied between the OPP and CPP layers base web: Polyethylene terephthalate (PET) 12μ/Oriented polypropylene (OPP) 20μ/Cast polypropylene 30μ. Any printing such as a white opaque printing can be placed between the PET layer and the OPP layer.

In one embodiment utilizing the above described film, a pinhole exposure to an oxygen environment caused the color of the indicator to change in less than three days to indicate the presence of oxygen. The indicator solution includes indigo carmine that changes from a yellow color when in reduced form which indicates a lack of oxygen to a blue when oxidized by the presence of oxygen.

The pouches are preferably constructed with a transparent portion to view the color of the indicating solution. The indicator solution is prepared under atmospheric conditions which means that the indicator is in its oxidized form and blue in color. During manufacturing the pouch containing the oxidized form of the indicator solution is placed in an overpouch with the container housing a TPN formulation and the overpouch is sealed and sterilized. During the sterilization cycle, the indicator solution is reduced and the solution turns yellow. The oxidation reduction reaction is shown below:

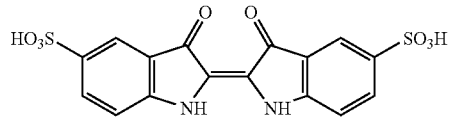 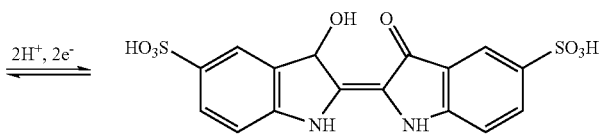

The reaction is reversible, i.e. the solution becomes blue again upon exposure to oxygen. In a preferred embodiment the indicators should be formed using components that would be non-toxic to the contents of the containers and to those users of the product who may be exposed to the indicator solution if there is a leakage through a breach in the film. In a more preferred embodiment, the components would consist of food additives that are well known for their non-toxicity.

An embodiment of an oxygen indicator is based on a 3 g/L indigo carmine concentration. The specific formulation is a mixture of 20 ml of 15% indigo carmine, 80 ml of 0.13M of sodium pyrophosphate and 18 g of microcrystalline cellulose and pH adjusted to 8.75 with HCl. The oxidized color of this currently available oxygen indicator produces a blue color when oxidized but this color degrades relatively quickly. After three months of storage at 40° C., the blue color fades to a skin color that it not distinct enough from the yellow color or reduced form of the indicator. This faded color would fail to provide unambiguous identification of exposure to oxygen. Similar results were observed for sample maintained at 30° C. for 8 months and 25° C. for 12 months.

In one attempt to overcome this shortcoming, the indigo carmine concentration was increased to 6 g/L concentration and compared to the currently available indicator (reference). The table below provides details of each formulation.

|  | Indigo carmine 1.5% | Sodium Pyrophosphate 0.13 M | Cellulose | HCl adjusted pH |
| --- | --- | --- | --- | --- |
| Reference | 20 mL | 80 mL | 18 g | 8.75 |
| Alternate1 | 40 mL | 60 mL | 30 g | 8.75 |

Since cellulose is provided to act as a reducing agent, the cellulose content was increased in this second embodiment (alternate 1) of indicator to compensate for the increase indigo carmine. In other words, more cellulose is needed to ensure the indicator reduces during sterilization.

Samples of each of the indicators were analyzed for their optical densities in absorption units (AU) at 610 nm, which is the absorbance range for the blue oxidized color, after formulation, sterilization and storage at a few temperatures over time. The results are show in the following table.

| Days | REF- 25° C. | REF- 30° C. | REF- 40° C. | ALT1- 25° C. | ALT1- 30° C. | ALT1- 40° C. |
| --- | --- | --- | --- | --- | --- | --- |
| 0 | 1.185 | 1.281 | 1.281 | 2.116 | 2.116 | 2.116 |
| 1 | 0.814 | 0.827 | 0.82 | 1.4614 | 1.3934 | 1.4246 |
| 15 |  |  |  | 1.3382 | 1.2337 | 1.1308 |
| 21 | 0.7162 | 0.603 | 0.2973 |  |  |  |
| 40 |  |  |  | 1.2816 | 1.1279 | 0.711 |
| 46 | 0.6312 | 0.4465 | 0.1168 |  |  |  |

-continued

| Days | REF-25° C. | REF-30° C. | REF-40° C. | ALT1-25° C. | ALT1-30° C. | ALT1-40° C. |
|---|---|---|---|---|---|---|
| 63 |  |  |  | 1.1903 | 1.1008 | 0.4358 |
| 69 | 0.5975 | 0.3726 | 0.0964 |  |  |  |
| 82 |  |  |  | 1.0662 | 0.9486 | 0.2445 |
| 87 | 0.5645 | 0.332 | 0.0574 |  |  |  |

Figure 12:
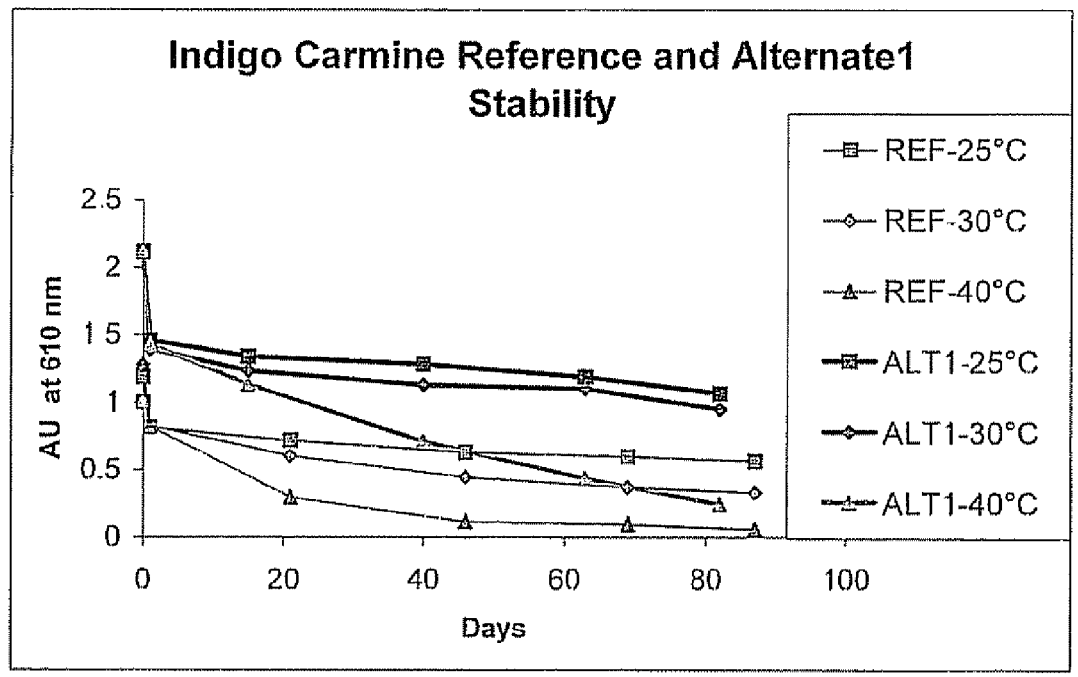
FIG. 12 is a graph representing Absorbance Units over time of the first and second embodiments of oxygen indicator stored at three different temperature conditions.

Day 0 means solution prior to sterilization while day 1 means solution after sterilization A graphical representation of the above date is shown in FIG. 12.

The initial absorbance after sterilization is about 1.4 AU with the alternate 1 formulation versus 0.8 AU for the first iteration. As shown on FIG. 9, the trend of decreasing in similar for both iterations. A longer stability of the oxidized color is expected but the expected 24 months' stability might be borderline with this formulation.

Other types of cellulose were also investigated using the reference indicator formulation, specifically DS-0 TLC cellulose, colloidal micro-crystalline cellulose, powder for chromatography cellulose, powder for chromatography acid washed cellulose, low and high viscosity carboxymethyl cellulose sodium salt, acetate cellulose and methyl cellulose. No major difference was observed between the formulations including other insoluble cellulose compounds. The testing did show that insoluble cellulose cannot be replaced by soluble grafted cellulose. In addition, EDTA was investigated as an additive known as a stabilizing agent. Again, the EDTA did not have a significant effect on the degradation of the oxidized color of the indicator.

Further increasing the concentration of the indigo carmine manufacturing complications caused by increasing the cellulose content and it was seen that increasing the level above the 300 g/L cellulose used in the alternate 1 indicator hampered manufacturability of the indicating pouch and created an undesirably paste like mixture. Any further increase would further exacerbate these issues and yet failure to increase the level of cellulose led to an inability to adequately reduce the higher levels of indigo carmine during sterilization.

It has been determined that adding an appropriate amount of a reducing agent and in a preferred example a stronger reducing sugar such as dextrose allows the indigo carmine concentration to be increased beyond the 6 g/L concentration while maintaining the cellulose content at the more preferred level of 180 g/L.

In one embodiment, the indicating solution includes, in addition to indigo carmine, a buffer for pH adjustment in the range of about 9.0 to about 9.75 prior to sterilization and from about 7.0 to about 9.0 after sterilization, cellulose and a reducing agent.

Indigo carmine is deemed as not a hazardous substance under European Community Directive 67/548/EEC. The concentration of indigo carmine can be greater than 6 g/l and less than about 60 g/L, preferably from about 10 to about 40 g/L, more preferably from about 14 to about 20 g/L with the lower concentration producing a more pleasing visual indicators. Concentrations of indigo carmine above 20 g/L further exceed the solubility limit and one would observe a lack of homogeneity in the color such as spots or clumps of dark color Buffers can include phosphate and acetate buffers. Specific buffers include sodium phosphate buffers and sodium acetate buffer with a preferred being sodium pyrophosphate buffer. Sodium pyrophosphate is deemed as not a hazardous substance under European Community Directive 67/548/EEC. Concentration of the sodium pyrophosphate buffer can be from about 0.11M to about 0.18M, preferably from 013M to about 017M. Other buffers may be suitable to arrive at the desired pH of 7-9 after sterilization. It has been observed that for the sterilization cycle being used for such nutritional products that a pH prior to sterilization of 9.0-100 will lead to the desired post sterilization pH.

Color and/or thickening agents can include insoluble cellulose compounds since it also has some reducing ability and is an approved food additive. Preferred cellulose is microcrystalline cellulose included at from about 150 to about 210 g/L, more preferably at about 180 g/L. Microcrystalline cellulose is deemed as not a hazardous substance under European Community Directive 67/548/EEC. Levels of cellulose up to 300 g/L were used but the mixture becomes a paste like mixture which creates issues in manufacturing using preferred equipment. It is envisioned that greater concentrations are feasible using other manufacturing techniques for producing the indicator.

An additional reducing agent is included such as one or more reducing sugars. A preferred reducing sugar can be dextrose although other reducing agents and sugars may be employed. However as previously described, in a preferred embodiment reducing sugars that are approved food additives are used. For example dextrose is a common ingredient used in infusion fluids. The concentration of the dextrose has to be adjusted in function of the indigo carmine concentration. It can be between about 1 and about 5 g/L of anhydrous dextrose, preferably from about 2 to about 4 g/L more preferably from about 2.5 to about 4 g/L. Higher levels of dextrose lead to a decrease in pH of the resultant mixture after sterilization which negatively impacts on the performance of the indicator.

In one embodiment of an indicator of the present invention, an indigo carmine mixture retains the yellow color and remains functional, i.e. changes from yellow to blue upon exposure to oxygen, after at least three months of storage at 40° C. and more preferably up to six months of storage at 40° C. In addition, once exposed to oxygen the oxidized form retains the blue color for at least three months of storage at 40° C. and more preferably up to six months of storage at 40° C.

In one embodiment, an indicator mixture is made by dissolving from about 14 to about 20 grams of indigo carmine in one liter of water, The water is preferably distilled. The mixture also include from about 2.5 to about 4.0 grams/L dextrose and from about 60 grams/L to about 75 grams/L tetrasodium pyrophosphate. A thickening agent acting as color enhancer and having reducing ability is included in the mixture such as, microcrystalline cellulose added at about 180 grams/L.

EXAMPLE 2

An indigo carmine indicator mixture was made as follows: 14 g indigo carmine, 60 g tetrasodium pyrophosphate, 2.75 g anhydrous dextrose, and 180 g microcrystalline cellulose were added to one liter of distilled water.

This mixture was placed in small pouches that were packed with oxygen absorber in an oxygen barrier overpouch and exposed to steam sterilization at 121° C. The samples were then stored in reduced form and the reduced form, i.e. yellow color of the indicator mixture, was still yellow after storage in a substantially oxygen free environment for 112 days at 50° C.

When similar packages were exposed to oxygen after being first placed in a reduced state as described above, the mixture changed to the oxidized form, i.e. dark blue color. The mixture remained dark blue after storage for 112 days at 50° C.

EXAMPLE 3

An indigo carmine indicator mixture was made as follows: 14 g indigo carmine, 60 g tetrasodium pyrophosphate, 2.00 g hydrous dextrose and 180 g microcrystalline cellulose were added to one liter of distilled waters. The results were similar to those found in Example 2 above.

EXAMPLE 4

A 14 g/L indigo carmine solution was made to determine the degradation kinetics of the blue color or oxidized form during a few months storage. The indicator was made by mixing 14 g of indigo carmine, 60 g of tetrasodium pyrophosphate, 2.5 g of anhydrous dextrose and 180 g of cellulose in one liter of distilled water.

Empty bags of nominal volume 50 ml were filled with this 14 g/L indicator formulation, then overpouched with oxygen absorber and sterilized. During sterilization, the color of the indicating mixture turns from blue (oxidized form) to yellow (reduced form).

Figure 13:
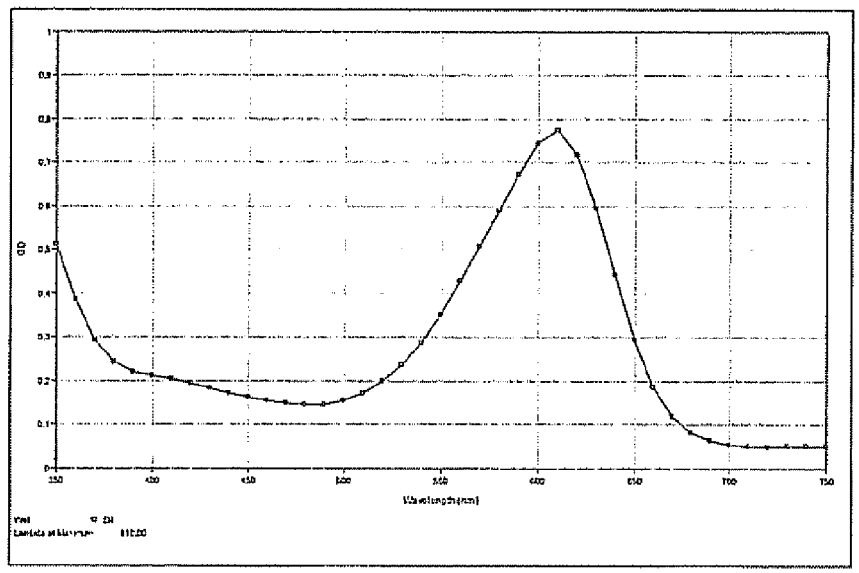
FIG. 13 is a graph of the optical densities of one embodiment of an oxygen indicator of the present invention.

The overpouch was then pierced and the indicating mixture was allowed to react with atmospheric oxygen under ambient conditions. Then the color of the indicating mixture turns back to blue (oxidized form). Using a syringe with a needle, a 1.0 ml of indicating mixture was withdrawn through the medication port of the container. This aliquot was diluted to 50 ml with water and the cellulose was removed by filtration or centrifugation. Finally, 200 µl of the solution were dispensed in a well of a polystyrene microtitration plate and the absorbance was recorded at 610 nm, i.e. the maximum wavelength at peak optical densities of the indigo carmine in its oxidized form. A graph of optical densities (O.D.), measured from 350 to 750 nm is shown in FIG. 13.

The test units were then stored at 25° C., 30° C. and 40° C. Samples were taken at several time intervals and spectrometric measurements were made. The following table shows the results:

| | Formulation with 14 g/l Optical density @ 610 nm (A.U.) | | |
|---|---|---|---|
| Days | T = 25° C. | T = 30° C. | T = 40° C. |
| 0 | 3.1118 | 2.9853 | 2.7592 |
| 0 | 3.0046 | 2.7807 | 2.7297 |
| 15 | 3.1118 | 2.9853 | 2.7592 |
| 15 | 3.0046 | 2.7807 | 2.7297 |
| 57 | 3.0515 | 2.9714 | 2.5663 |
| 57 | 2.9727 | 2.8054 | 2.3863 |
| 130 | 2.7753 | 2.6868 | 2.3288 |
| 130 | 2.7006 | 2.6237 | 2.0991 | note:
P0 measurements are not available and P15 measurements were therefore reported at P0

Figure 14:
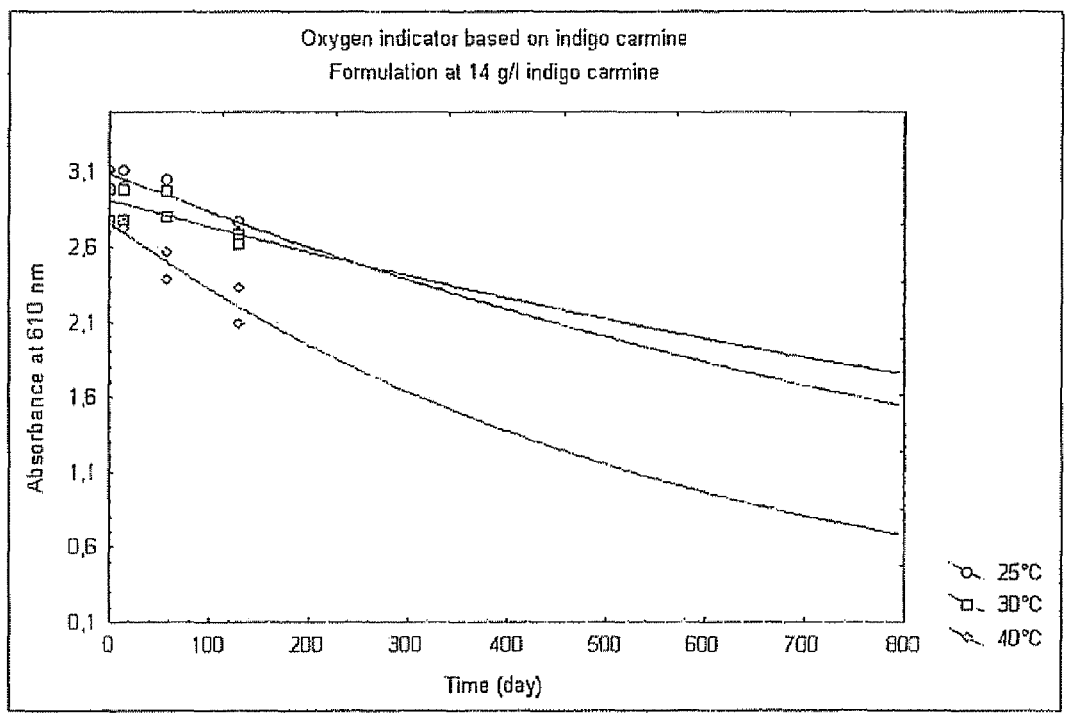
FIG. 14 is a graph of Absorbance Units over time of one embodiment of an oxygen indicator of the present invention fit in an exponential curve.

These data fit an exponential curve which is shown in FIG. 14.

The values recorded up to 130 days indicate that the oxidized color is acceptable after 3 months at the three temperatures and that the six months stability of the oxidized blue color will most likely be reached at the three storage temperatures.

EXAMPLE 5

An indigo carmine indicator mixture was made as follows: 20 g indigo carmine, 75 g tetrasodium pyrophosphate, 4.0 g anhydrous dextrose and 180 g microcrystalline cellulose were added to one liter of distilled water. This mixture was placed in small pouches that were packed with oxygen absorber in an oxygen barrier overpouch and exposed to steam sterilization at 121° C. The samples were then stored in reduced form and the reduced form, i.e. yellow color of the indicator mixture, was still yellow after storage in a substantially oxygen free environment for 112 days at 50° C.

When similar packages were exposed to oxygen after being first placed in a reduced state as described above, the mixture changed to the oxidized form, i.e. dark blue color. The mixture remained dark blue after storage for 112 days at 50° C.

Spectrographic analysis was conducted on the oxidized form of this indicating mixture (20 g/l) in the same manner described with regards to the formulation with 14 g/L indigo carmine and the results are shown in the following table:

| | Formulation with 20 g/l Optical density @ 610 nm (A.U.) | | |
|---|---|---|---|
| Days | T = 25° C. | T = 30° C. | T = 40° C. |
| 0 | 3.434 | 3.473 | 3.465 |
| 7 | 3.4463 | 3.5024 | 3.6194 |
| 51 | 3.5678 | 3.5471 | 4.0000 |
| 124 | 3.5293 | 3.5593 | 4.0000 |
| After ¹/₁₀ dilution | | | |
| 0 | 0.606 | 0.683 | 0.634 |
| 7 | 0.613 | 0.562 | 0.620 |
| 51 | 0.731 | 0.711 | 0.646 |
| 124 | 0.631 | 0.626 | 0.572 |

Figure 15:
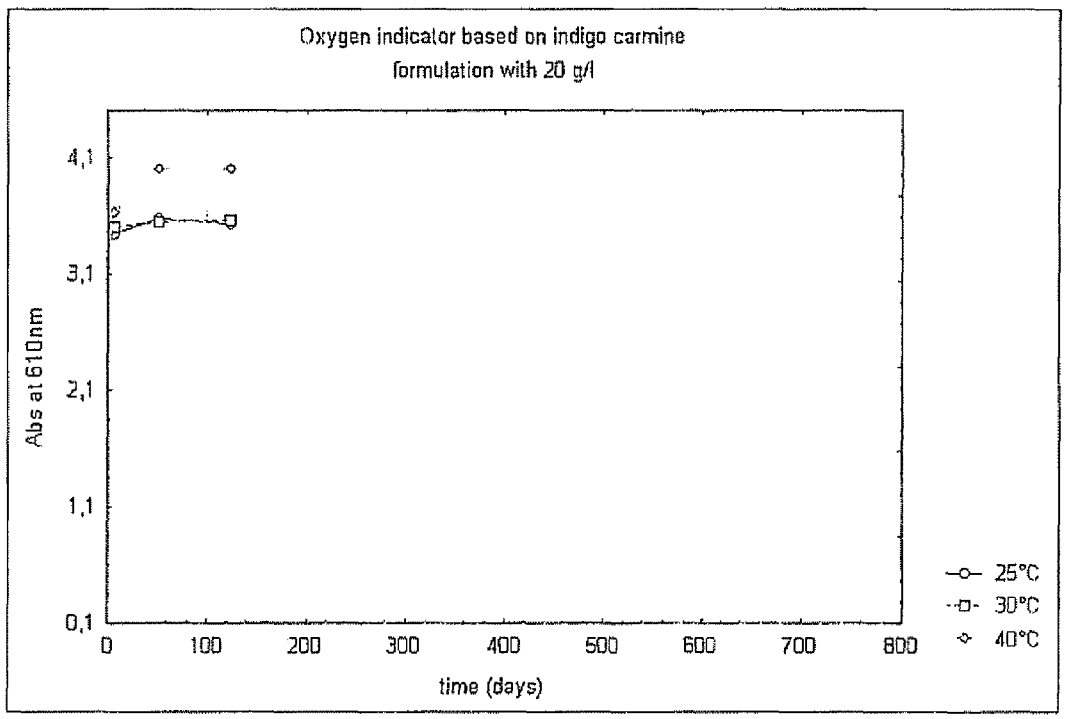
FIG. 15 is a graph representing Absorbance Units over time of one embodiment of an oxygen indicator of the present invention stored at three different temperature conditions.

The results are also represented graphically in FIG. 15.

According to the absorbance data this 20 g/L formulation showed no degradation of the oxidized color after 124 days, but this may be due to saturation of the detector as absorbance values approach 4 A.U. in conjunction with some water loss. When samples are diluted 10 times, a slight decreasing trend in absorbance is observed at 40° C. but again, the results indicate that the 6 months stability of the oxidized blue color at 40° C. will be reached with this formulation.

EXAMPLE 6

Long term stability studies were then conducted to show that the indicators would function over the desired shelf life of the products which would be employing the indicator. Two liters of a 14 g/L indigo carmine indicator and a 20 g/L indigo carmine indicator formulation were made to determine indicator activity and color degradation. The 14 g/L formulation was made by dissolving 120 g of sodium pyrophosphate in 2000 ml of water. In this solution 28 g of indigo carmine was added followed by 5 g of anhydrous dextrose. The solution was stirred for a few minutes to maximize the dissolution of indigo carmine. 360 g of cellulose was then added. The pH was measured but not adjusted. The pH should be above 9.4. The 20 g/L formulation was made by dissolving 150 g of sodium pyrophosphate in 2000 ml of water. In this solution 40 g of indigo carmine was added followed by 8 g of anhydrous dextrose. The solution was stirred for a few minutes to maximize the dissolution of indigo carmine 360 g of cellulose was then added. The pH was measured but not adjusted. The pH should be above 9.4.

A large number of small pouches were produced with half of which were filled with about 0.2 ml of the 14 g/L indicator formulation and the other half with the 20 g/L indicator formulation. These indicator pouches were then placed in separate overpouches containing multi-chambered bags of water. Half of the overpouches containing the 14 g/L indicators were heat sterilized using a short heat sterilization procedure, specifically 27 minutes exposure at 121° C. to determine if the indicators would change from the oxidized form (blue color) to the reduced form (yellow color) and the other half of the 14 g/L indicator were heat sterilized using a long heat sterilization procedure specifically +42 minutes exposure at 122° C. to test the stability of the both the reduced color and oxidized color. The same was performed on the overpouches containing the 20 g/L indicators.

Half of the samples or each lot were exposed to oxygen by piercing the overpouch using a 21G needle to create a pinhole. The all these indicators in these exposed samples then turned blue.

All of the samples were divided and stored in controlled climatic rooms. One of the rooms was maintained at 25° C., and 40% relative humidity, a second room was maintained at 30° C., 35% relative humidity, and a third room was maintained at 40° C., 25% relative humidity. These rooms were maintained at these conditions with a tolerance of ±2° C. for temperature and .+−0.5% for relative humidity. Samples maintained at 40° C. were tested at 0, 2, 4, 6 months and samples in the 25° C. and 30° C. rooms were tested at 0, 2, 4, 6, 9, 12, 15, months for each storage condition. The samples were visually inspected and categorized at the closest PANTONE® color reference via the PANTONE® color formula guide—solid coated (second edition 2004) for each period and at each temperature. At each testing period a subset of the stored samples was selected from the exposed lots and the unexposed lots from each room. The indicator from the exposed lot was examined to determine whether the indicator still indicated the presence of oxygen by displaying a blue color. The non-exposed samples were initially examined to determine if the indicator still indicated the absence of oxygen, then the overpouch was pierced with the 21 G needle to allow oxygen to flow into the overpouched product and the indicators were observed for a color shift sufficient to show the presence of oxygen.

In summary, at 40C and 6 months all of the samples of oxygen indicators performed as desired. All of the exposed samples continued to display a bluish color sufficient to indicate the presence of oxygen. All of the non-exposed samples displayed the yellowish color to indicate the absence of oxygen. When the overpouch was pierced, all of the now exposed, non-exposed samples changed to the bluish color sufficient to indicate the presence of oxygen. After 6 months the testing at 40C was concluded.

Similar results were found in the samples kept at 25C and 30 C at the 2, 4, 6, 9, 12, 15 month intervals. Exposed samples continued to display a color indicating the presence of oxygen and non-exposed sample continued to display a color indicating the absence of oxygen. When the non-exposed samples were then exposed to oxygen by penetration of the overpouch with a needle, the samples changed colors to indicate the presence of oxygen within 67 hours.

Figure 16:
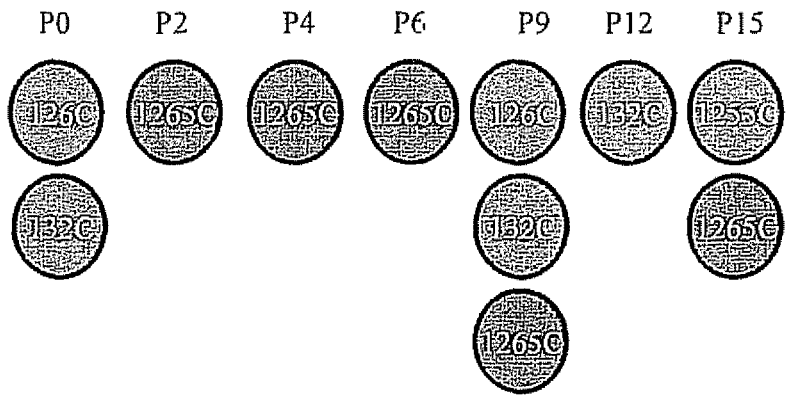
FIG. 16 shows the colors of the reduced form of samples of an oxygen indicator of the present invention stored at 25° C./40% RH and categorized by PANTONE® color references.
Figure 17:
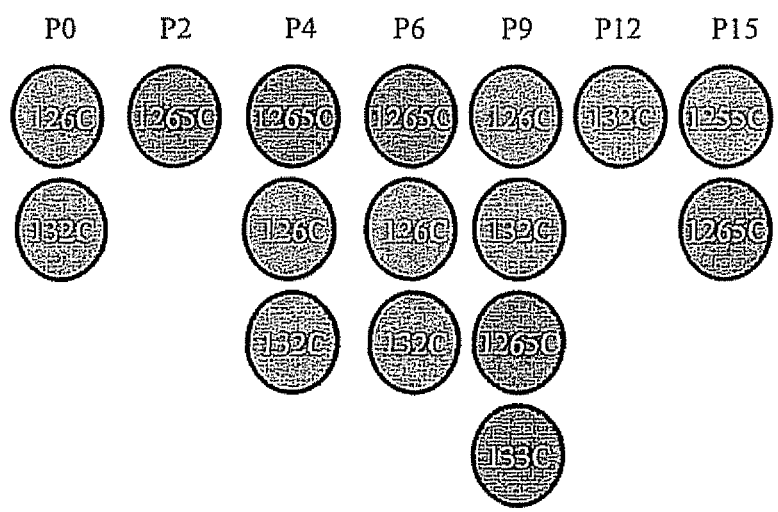
FIG. 17 shows the colors of the reduced form of samples of an oxygen indicator of the present invention stored at 30° C./35% RH and categorized by PANTONE® color references.
Figure 18:
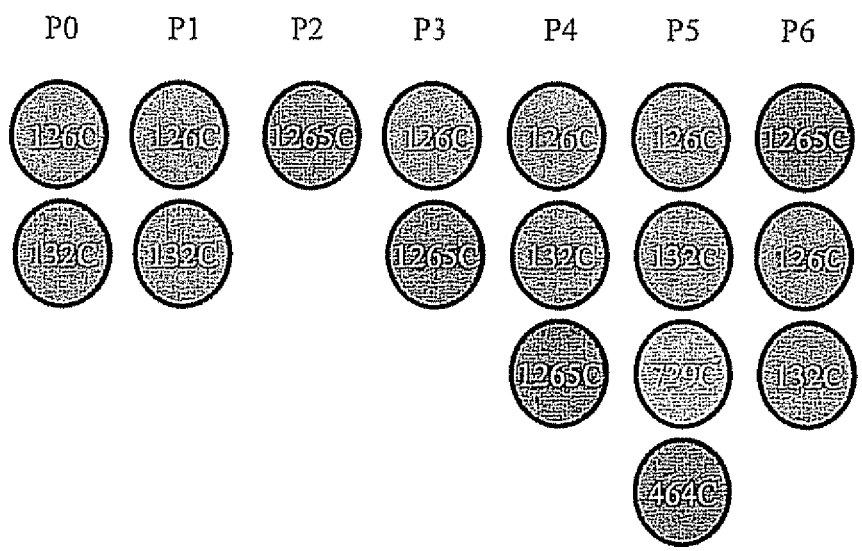
FIG. 18 shows the colors of the reduced form of samples of an oxygen indicator of the present invention stored at 40° C./25% RH and categorized by PANTONE® color references.
Figure 19:
FIG. 19 shows the colors of the reduced form of samples of an oxygen indicator of the present invention after illumination of 2000 lux with a daylight tube for 30 days at 25° C. and categorized by PANTONE® color references.

The results are shown in FIGS. 16, 17 and 18, which indicate the reduced color of the oxygen units, did not vary significantly after 6 months storage under any of the storage conditions tested.

Figure 20:
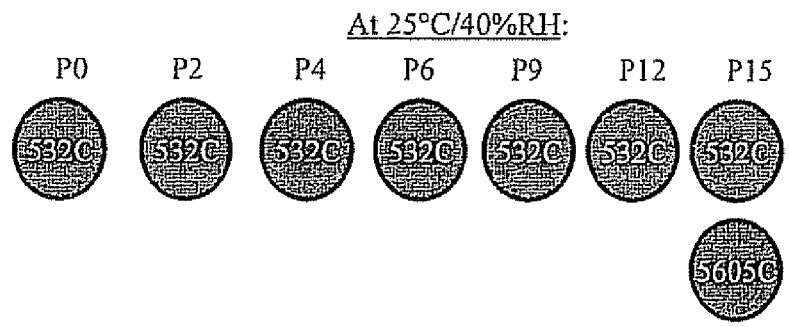
FIG. 20 shows the colors of the oxidized form of samples of an oxygen indicator of the present invention stored at 25° C./40% RH and categorized by PANTONE® color references.

After sterilization two units per formulation per sterilization cycle (8 units total) were exposed to constant illumination of 2000 lux with TL tube (tube daylight) for 30 days at 25° C., using a light box. The PANTONE® color references are shown in FIG. 20 which indicate the formulations were not deteriorated by light exposure.

Figure 21:
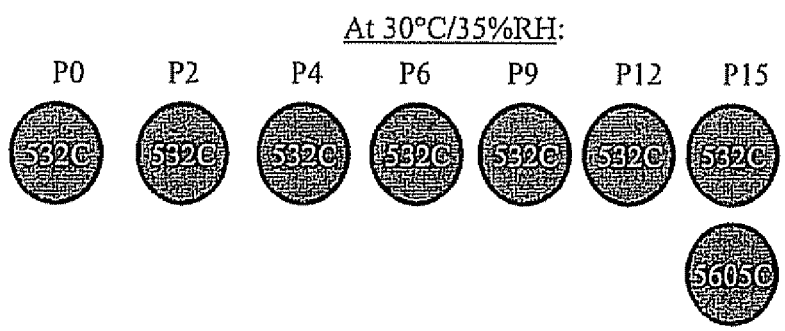
FIG. 21 shows the colors of the oxidized form of samples of an oxygen indicator of the present invention stored at 30° C./35% RH and categorized by PANTONE® color references.
Figure 22:
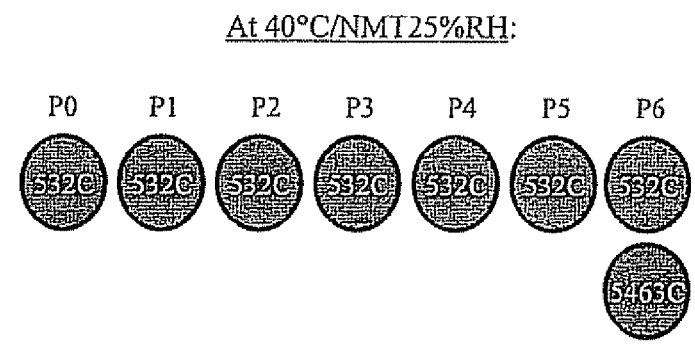
FIG. 22 shows the colors of the oxidized form of samples of an oxygen indicator of the present invention stored at 40° C./25% RH and categorized by PANTONE® color references.

A pinhole was pierced in the overpouch using a 21G needle of all the units including the illuminated units. All units turned blue after puncturing within 1 to 67 hours. The closest PANTONE® color reference was estimated at each temperature and period and the results for each temperature and period are shown in FIGS. 20, 21, 22 which indicate the oxidized color of the oxygen units, did not vary significantly after 6 months storage under any of the storage conditions tested.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

We claim:

1. A flexible multilayer bag for storing and admixing medical products comprising:
   a) top, bottom, first and second lateral sides;
   b) a first chamber, a middle chamber, and a third chamber, the middle chamber having a longitudinal length that is from about two-thirds to about three-quarters of longitudinal lengths of the first and third chambers;
   c) a first frangible barrier separating the first and middle chambers and a second frangible barrier separating the middle and third chambers;
   d) a flap defining straight borders of upper ends of the first chamber, middle chamber and third chamber; and
   e) at least two ports located at the bottom side, each port providing access to a different one of the first, middle, and third chambers wherein the first, middle and third chambers are arranged such that rolling the bag from the top side allows selective activation of one of the first and second frangible barriers without activating the other of the first and second frangible barriers.

2. The flexible multilayer bag of claim 1 wherein the first and second frangible barriers are peelable seals.

3. The multilayer bag of claim 1 further including three ports, each port providing fluid communication with a different one of the first, middle, and third chambers.

4. The multilayer bag of claim 3 further including a component of a parenteral formulation for fluid restricted patients in each of the first, middle and third chambers wherein one of the components includes cysteine.

5. The multilayer bag of claim 4 wherein the flap includes an opening for hanging the multilayer bag on a stand or hook.

6. The flexible multilayer bag of claim 1, wherein the first chamber is positioned adjacent to one of the first and second lateral sides, and wherein the third chamber is positioned adjacent the other of the first and second lateral sides.

7. A flexible multilayer bag for storing and admixing medical products comprising:
   a) top, bottom, left, and right sides;
   b) a first chamber, a second chamber, and a third chamber, the first and second chambers having longitudinal lengths that differ from each other by a degree of about twenty five percent to about thirty three percent, the second and third chambers having longitudinal lengths that differ from each other by a degree of about twenty five percent to about thirty three percent;
   c) a plurality of frangible barriers separating the first, second and third chambers from each other;
   d) a flap defining a straight border of upper ends of the first, second and third chambers; and e) at least two ports located at the bottom side, each port providing access to a different one of the first, second, and third chambers wherein the first, second and third chambers are arranged such that rolling the bag starting at an intersection between the top side and one of the left and right sides allows selective activation of one of the frangible barriers without activating the other of the frangible barriers.

8. The flexible multilayer bag of claim 7 wherein the plurality of frangible barriers are peelable seals.

9. The flexible multilayer bag of claim 7 further including a third port providing fluid communication with the other of the first and second chambers.

10. The flexible multilayer bag of claim 7, wherein the first chamber is positioned adjacent to one of the left and right sides, and wherein the third chamber is positioned adjacent to the other of the left and right sides.

* * * * *